(12) United States Patent
Kobayashi et al.

(10) Patent No.: US 10,973,473 B2
(45) Date of Patent: Apr. 13, 2021

(54) X-RAY DIAGNOSTIC APPARATUS

(71) Applicant: Canon Medical Systems Corporation, Otawara (JP)

(72) Inventors: Yoshimasa Kobayashi, Nasushiobara (JP); Kazunari Shima, Utsunomiya (JP); Hayato Kasaoka, Nasushiobara (JP); Takahiro Tanaka, Nasushiobara (JP); Hisanori Kato, Otawara (JP); Nobuo Kobayashi, Nasushiobara (JP); Norimitsu Kosugi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 302 days.

(21) Appl. No.: 16/014,701

(22) Filed: Jun. 21, 2018

(65) Prior Publication Data

US 2018/0368788 A1 Dec. 27, 2018

(30) Foreign Application Priority Data

Jun. 27, 2017 (JP) .............................. JP2017-125322
Jun. 27, 2017 (JP) .............................. JP2017-125325

(51) Int. Cl.
*A61B 6/06* (2006.01)
*A61B 6/00* (2006.01)
(Continued)

(52) U.S. Cl.
CPC ................. *A61B 6/06* (2013.01); *A61B 6/08* (2013.01); *A61B 6/461* (2013.01); *A61B 6/465* (2013.01);
(Continued)

(58) Field of Classification Search
CPC .. A61B 6/06; A61B 6/08; A61B 6/461; A61B 6/465; A61B 6/469; A61B 6/50;
(Continued)

(56) References Cited

U.S. PATENT DOCUMENTS 2,922,046 A * 1/1960 Billin ..................... G21K 1/025
378/155
4,329,590 A * 5/1982 Adelmeyer .......... A61B 6/4476
378/151
(Continued)

FOREIGN PATENT DOCUMENTS

| JP | 2007-159913 | 6/2007 |
| JP | 2011-224331 | 11/2011 |
| JP | 2014-184340 | 10/2014 |

*Primary Examiner* — Blake C Riddick
(74) *Attorney, Agent, or Firm* — Oblon, McClelland, Maier & Neustadt, L.L.P.

(57) ABSTRACT

According to one embodiment, an X-ray diagnostic apparatus includes an X-ray movable diaphragm and processing circuitry. The X-ray movable diaphragm limits an irradiation field of an X-ray. The processing circuitry sets an FOV size related to the irradiation field, sets a virtual field of view having the FOV size, the virtual field of view being able to include an outside region of an X-ray detection region and at least a part of the X-ray detection region, and controls the X-ray movable diaphragm so as to apply the X-ray to a common region between the virtual field of view and the X-ray detection region.

22 Claims, 24 Drawing Sheets

(51) Int. Cl.
*G06T 3/40* (2006.01)
*G06T 7/00* (2017.01)
*A61B 6/08* (2006.01)

(52) U.S. Cl.
CPC ............... *A61B 6/469* (2013.01); *A61B 6/50* (2013.01); *A61B 6/5294* (2013.01); *A61B 6/54* (2013.01); *A61B 6/542* (2013.01); *A61B 6/544* (2013.01); *G06T 3/403* (2013.01); *G06T 7/0014* (2013.01); *A61B 6/467* (2013.01); *A61B 6/5205* (2013.01); *G06T 2207/10121* (2013.01)

(58) Field of Classification Search
CPC ......... A61B 6/5294; A61B 6/54; A61B 6/542; A61B 6/544; A61B 6/467; A61B 6/5205; G06T 3/403; G06T 7/0014; G06T 2207/10121
See application file for complete search history.

(56) References Cited

U.S. PATENT DOCUMENTS

| | | | | |
|---|---|---|---|---|
| 5,924,987 A * | 7/1999 | Meaney | ............... | A61B 5/055 600/420 |
| 6,549,268 B1 * | 4/2003 | Nishi | ............... | G03F 9/7015 355/53 |
| 2002/0141531 A1 * | 10/2002 | Taguchi | ............... | G01N 23/046 378/19 |
| 2003/0031290 A1 * | 2/2003 | Sugihara | ............... | A61B 6/032 378/15 |
| 2004/0125151 A1 * | 7/2004 | Hamilton | ............... | G09B 9/24 715/848 |
| 2004/0240604 A1 * | 12/2004 | Wang | ............... | A61B 6/027 378/19 |
| 2006/0140483 A1 * | 6/2006 | Jabri | ............... | G06K 9/3216 382/199 |
| 2007/0133747 A1 * | 6/2007 | Manak | ............... | A61B 6/542 378/62 |
| 2009/0080618 A1 * | 3/2009 | Kosugi | ............... | A61B 6/04 378/146 |
| 2009/0245464 A1 * | 10/2009 | Yamaguchi | ............... | A61B 6/4441 378/62 |
| 2009/0304141 A1 * | 12/2009 | Nakazawa | ............... | A61B 6/032 378/5 |
| 2011/0240872 A1 | 10/2011 | Sawada et al. | | |
| 2012/0243655 A1 * | 9/2012 | Ninomiya | ............... | A61B 6/027 378/8 |
| 2013/0315372 A1 * | 11/2013 | Behiels | ............... | A61B 6/4216 378/62 |
| 2014/0205163 A1 * | 7/2014 | Stark | ............... | A61B 6/467 382/128 |
| 2015/0297166 A1 * | 10/2015 | Goto | ............... | A61B 6/5205 378/15 |
| 2015/0342544 A1 * | 12/2015 | Funabasama | ............... | A61B 6/542 378/8 |
| 2016/0051210 A1 * | 2/2016 | Kojima | ............... | A61B 6/06 378/62 |
| 2016/0242710 A1 * | 8/2016 | Grbic | ............... | A61B 6/485 |
| 2017/0340903 A1 * | 11/2017 | Ie | ............... | A61N 5/1081 |
| 2018/0333127 A1 * | 11/2018 | Ahn | ............... | A61B 6/032 |

* cited by examiner

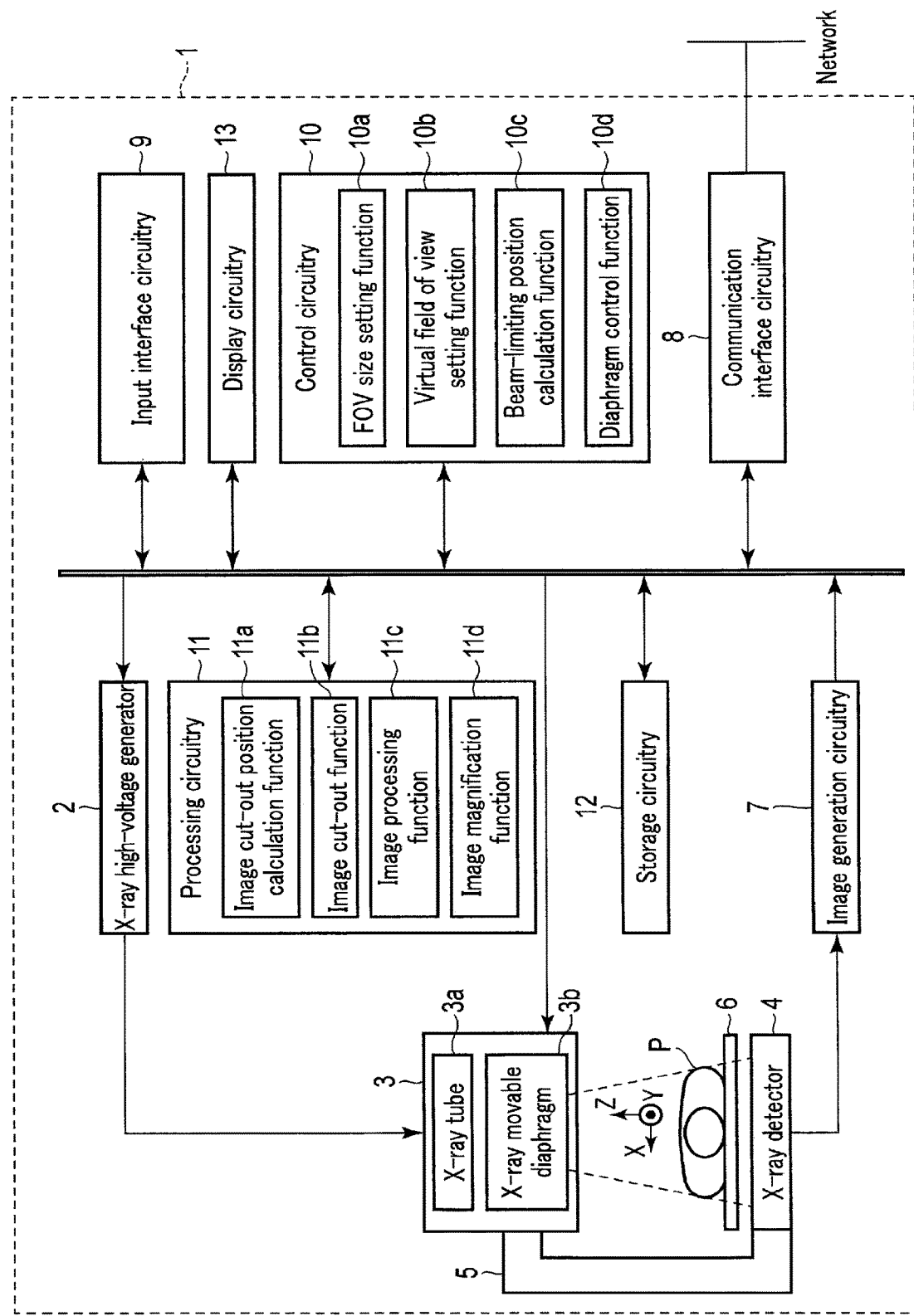
F I G. 1

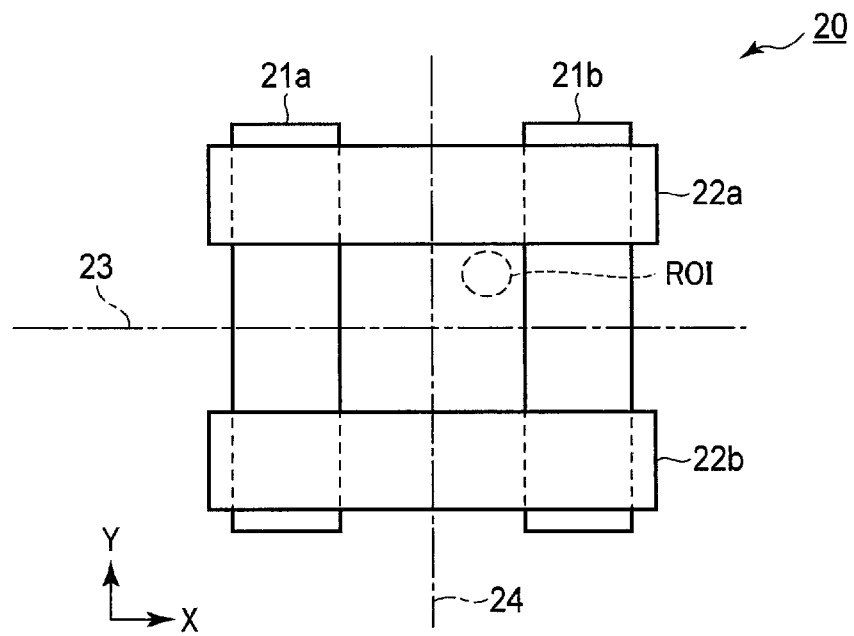
F I G. 2
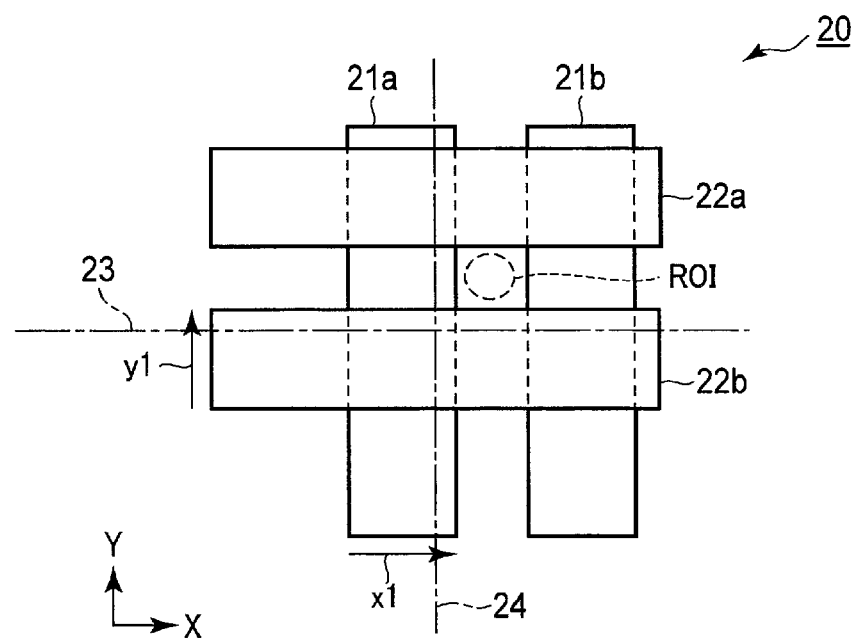
F I G. 3

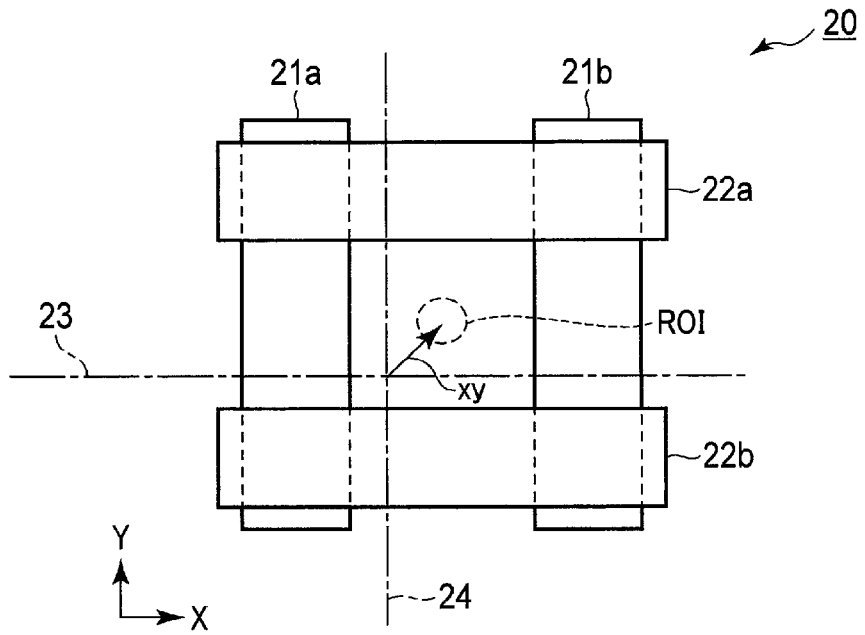
F I G. 4A
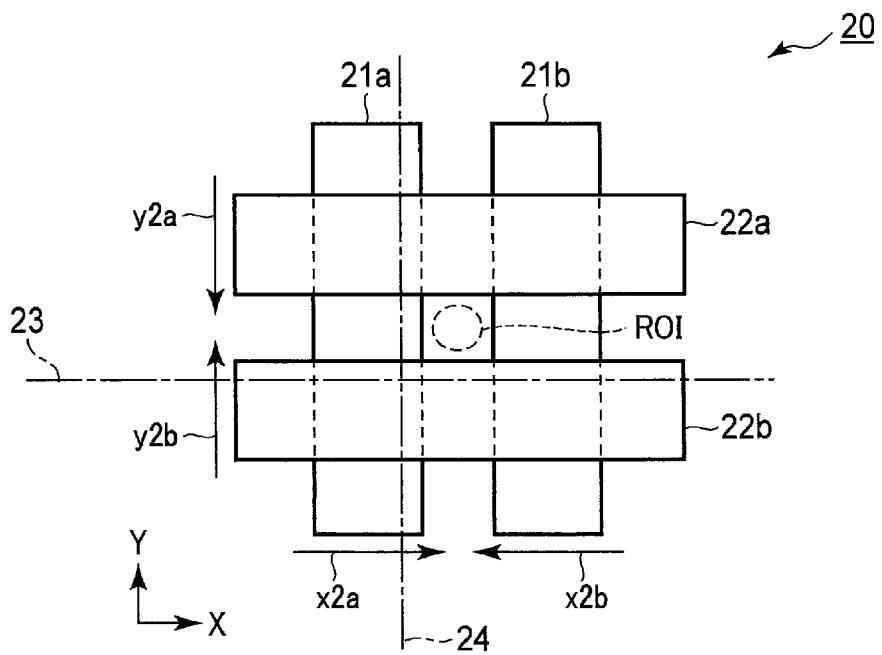
F I G. 4B

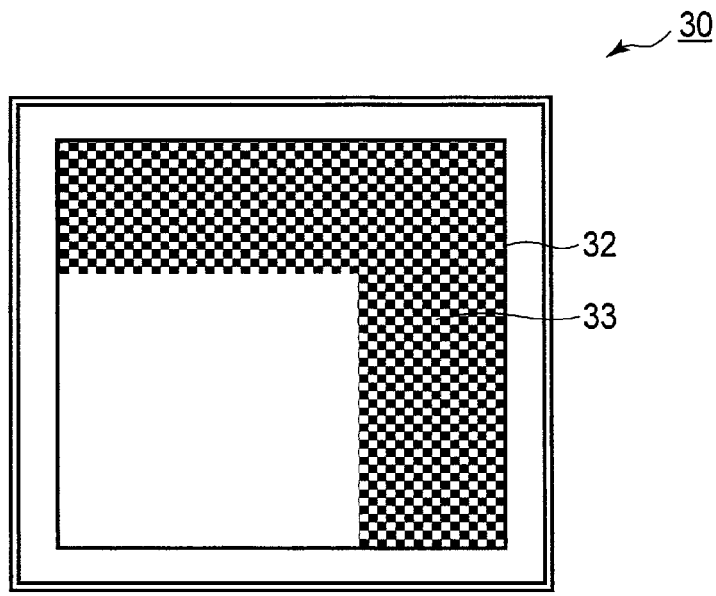
F I G. 8B
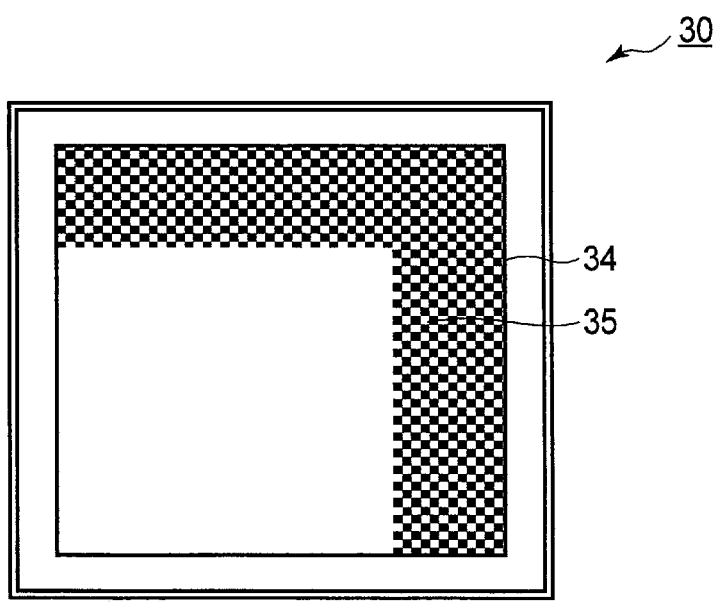
F I G. 8C

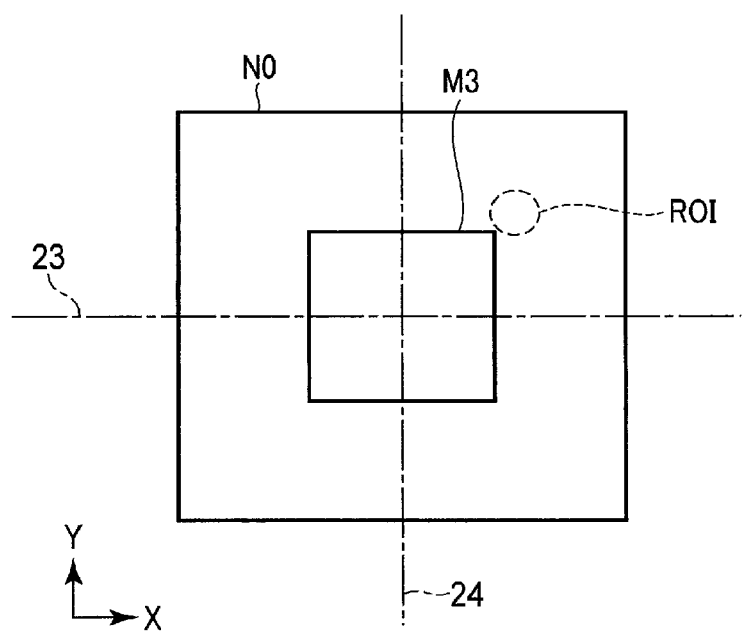
F I G. 9A

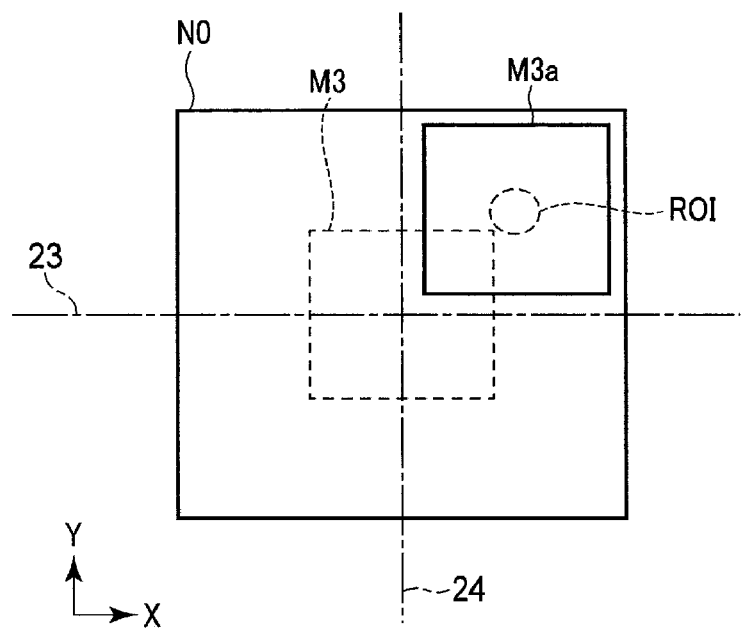
F I G. 9B
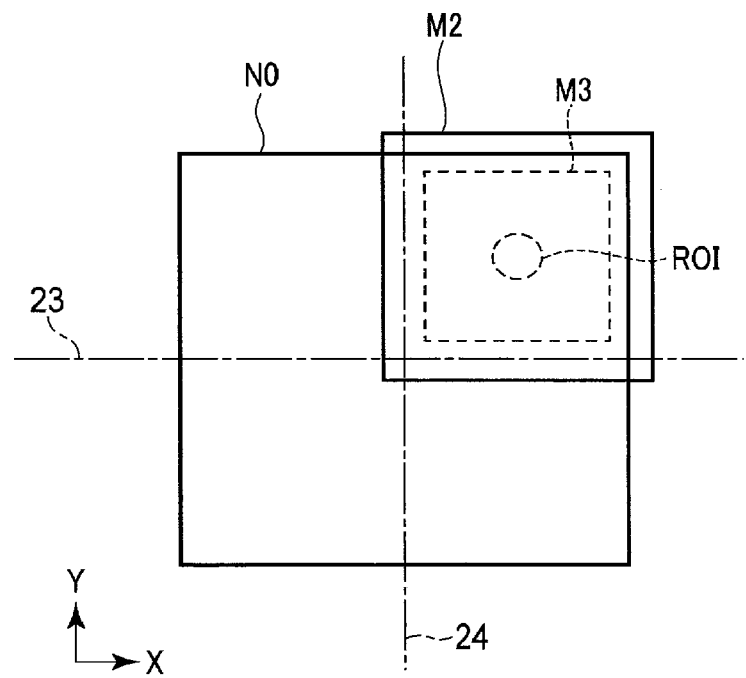
F I G. 9C

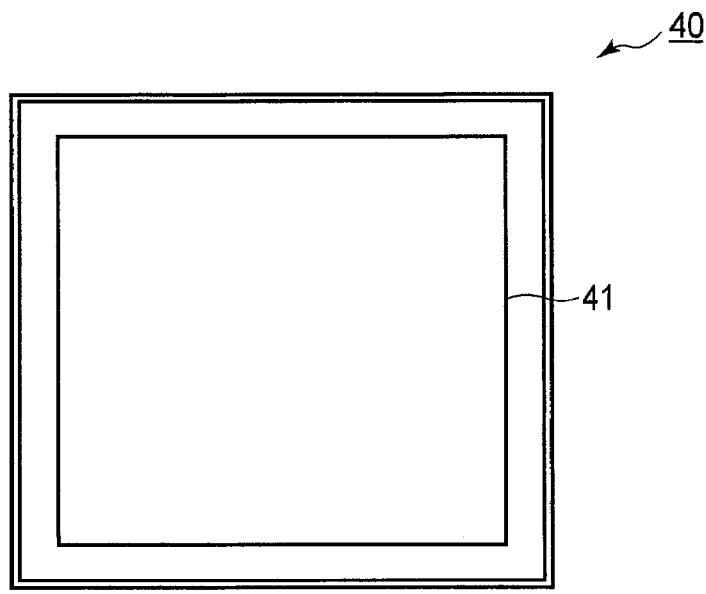
F I G. 10A
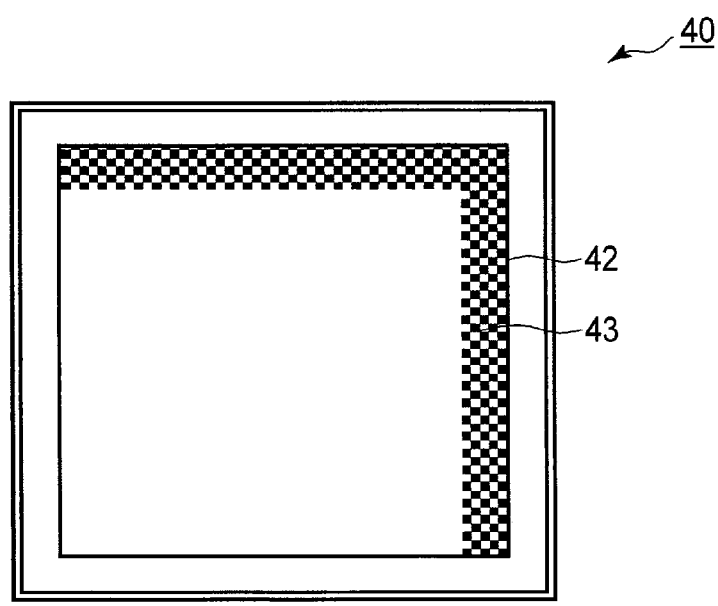
F I G. 10B

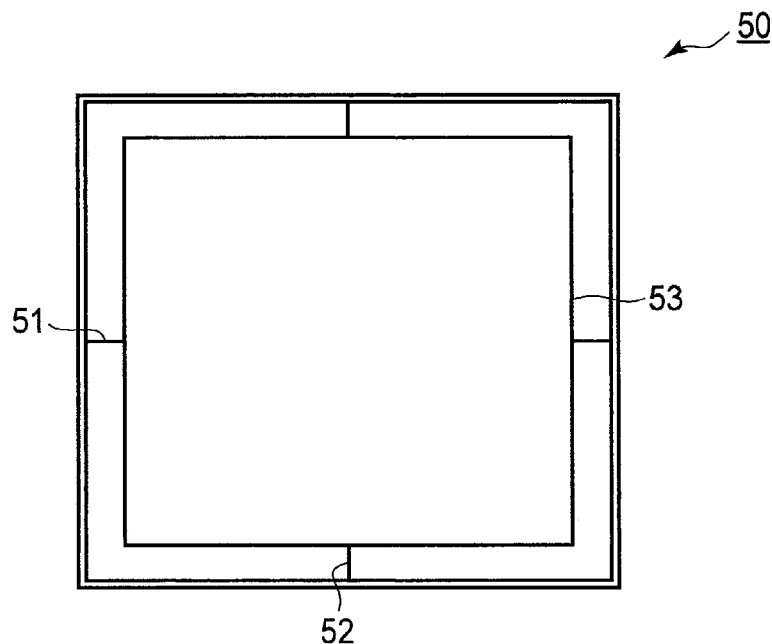
F I G. 11A
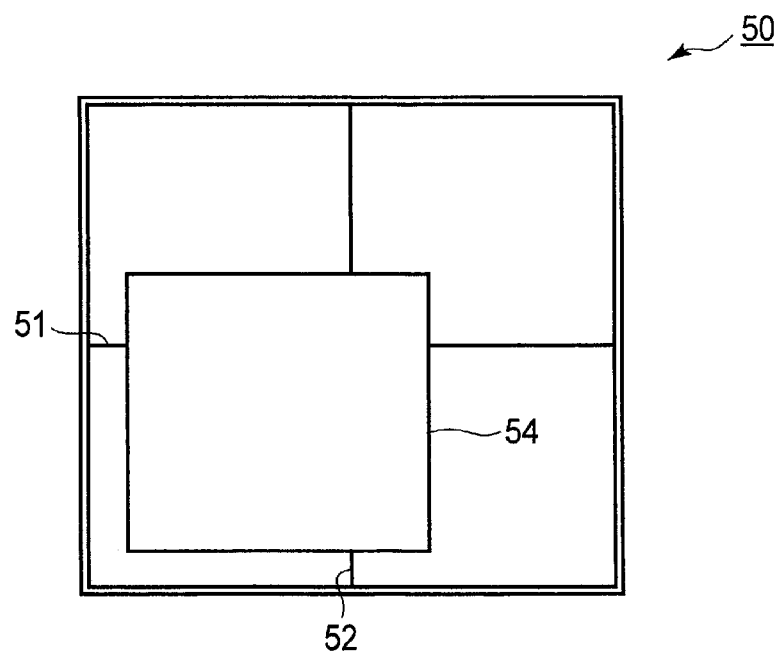
F I G. 11B

| FOV Size | FOV Position |
|---|---|
| N0 | (x0,y0) |
| M1 | (x1a,y1a) |
| M2 | (x2a,y2a) |
| M3 | (x3a,y3a) |

F I G. 13A

| FOV Size | FOV Position | X-ray Conditions |
|---|---|---|
| N0 | (x0,y0) | XC0 |
| M1 | (x1a,y1a) | XC1 |
| M2 | (x2a,y2a) | XC2 |
| M3 | (x3a,y3a) | XC3 |

F I G. 13B

| FOV Size | FOV Position a | FOV Position b | FOV Position c |
|---|---|---|---|
| N0 | (x0,y0) | (x0,y0) | (x0,y0) |
| M1 | (x1a,y1a) | (x1b,y1b) | (x1c,y1c) |
| M2 | (x2a,y2a) | (x2b,y2b) | (x2c,y2c) |
| M3 | (x3a,y3a) | (x3b,y3b) | (x3c,y3c) |

F I G. 13C

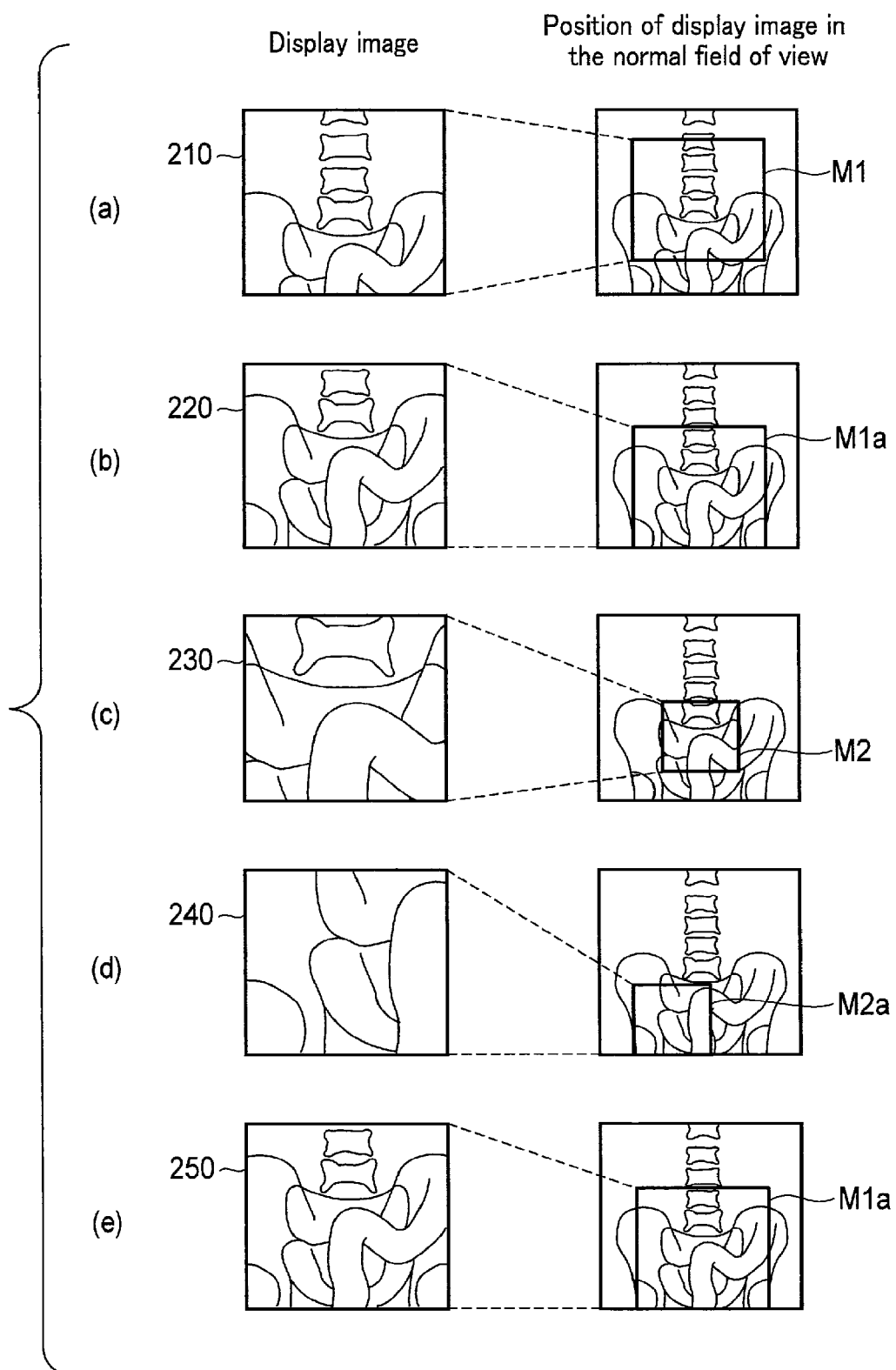
F I G. 15

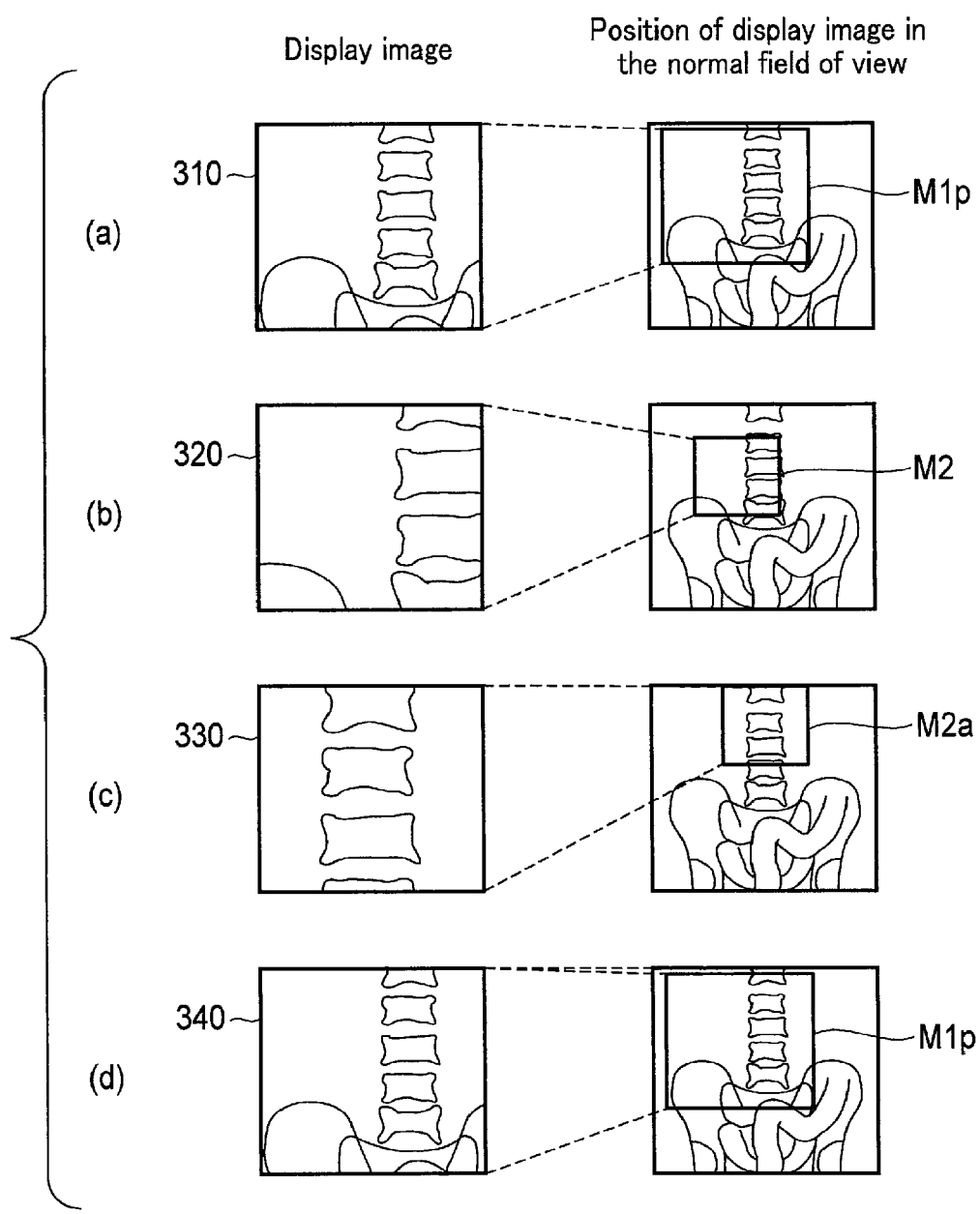
F I G. 18

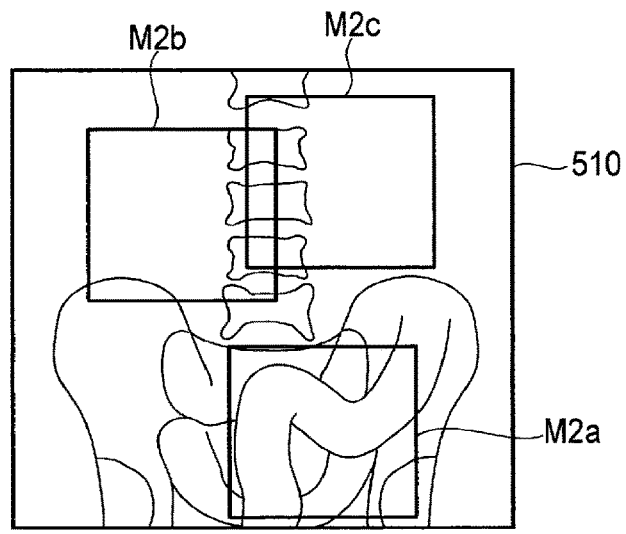
F I G. 19
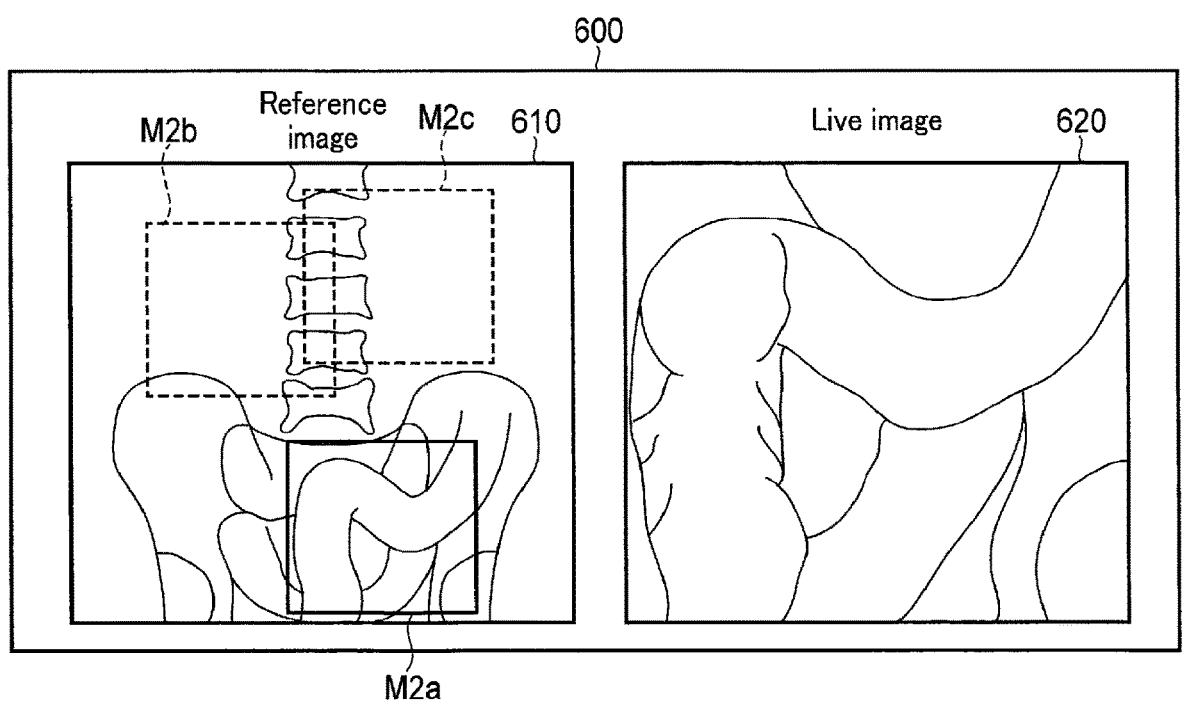
F I G. 20

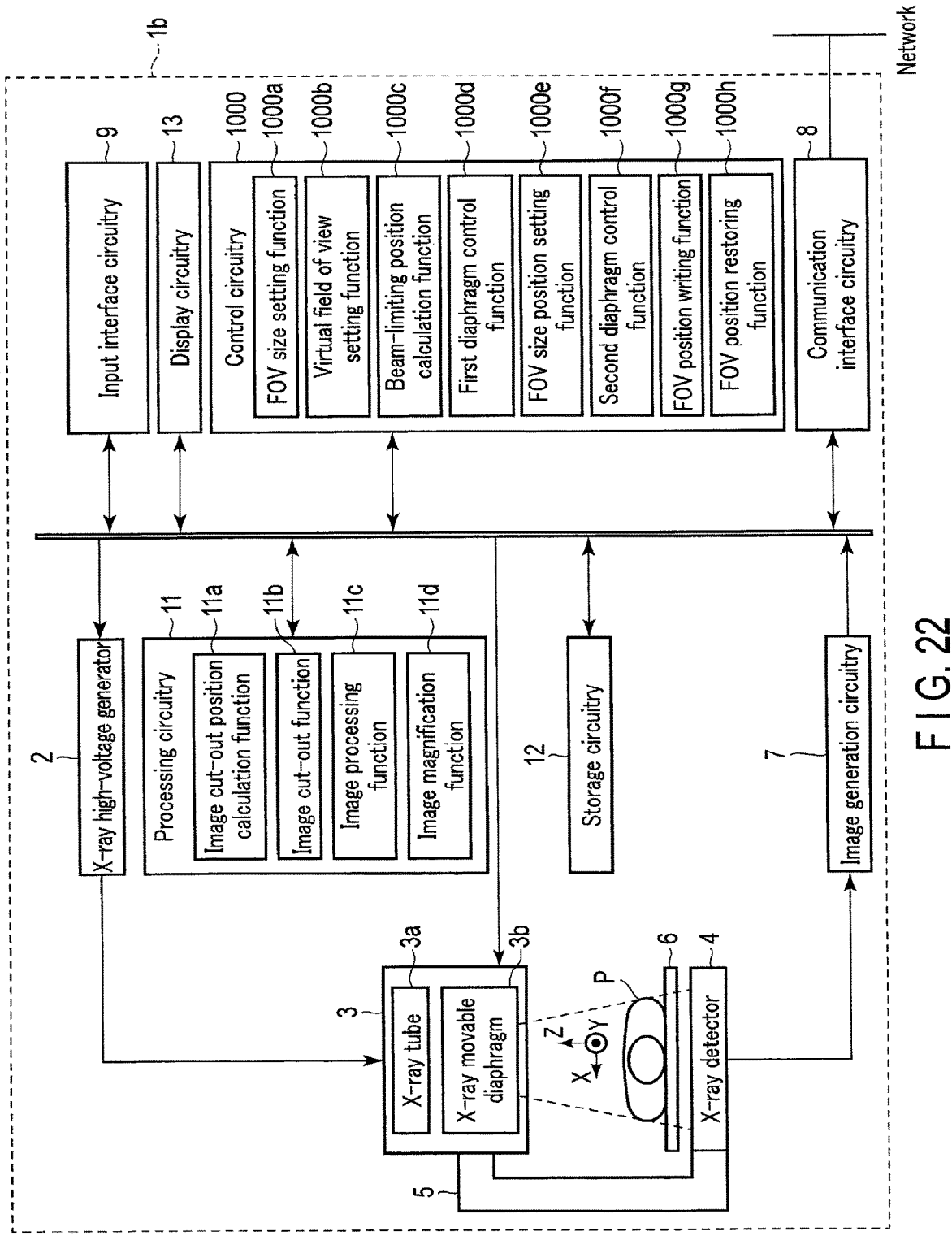
F I G. 22

X-RAY DIAGNOSTIC APPARATUS

CROSS-REFERENCE TO RELATED APPLICATIONS

This application is based upon and claims the benefit of priority from Japanese Patent Applications No. 2017-125322, filed Jun. 27, 2017; and No. 2017-125325, filed Jun. 27, 2017; the entire contents of both of which are incorporated herein by reference.

FIELD

Embodiments described herein relate generally to an X-ray diagnostic apparatus.

BACKGROUND

In general, an X-ray diagnostic apparatus sets a field of view in a discretional range of an X-ray detection region of an X-ray detector and controls an X-ray movable diaphragm so as to apply X-ray only to this range. Thereafter, the X-ray diagnostic apparatus displays an image based on the X-ray detected in the range where the X-ray is applied. Such an X-ray diagnostic apparatus has a function to change a magnification ratio of a display image, with a central focus on a region of interest.

There is no problem when an X-ray diagnostic apparatus as described above is used in normal conditions; however, according to the inventor's consideration, when X-ray is applied to the end of an X-ray detection region, there is a disadvantage that a region of interest is not always positioned in a center portion of a display image. For example, when a region of interest is positioned at the end of an X-ray detection region, the field of view is set so as not to include the outer side of the X-ray detection region from the viewpoint of avoiding applying the X-ray to the outer side of the X-ray detection region. For this reason, when the X-ray should be applied to the end of the X-ray detection region, the region of interest is positioned at the end of the display image.

Also, for example, even when a region of interest is positioned at the center of a display image corresponding to a certain field of view size (hereinafter, referred to as FOV size), if the FOV size is widened to the outer side of an X-ray detection region due to the magnification of the FOV size, the magnified field of view of the FOV size is forcibly set within the X-ray detection region. For this reason, when X-ray is applied to the end of the X-ray detection region, the display image becomes an image where the region of interest is positioned out of the center of the display image, while maintaining the magnified FOV size.

Incidentally, presently, there is a technique of setting a field of view at a field of view position (hereinafter, referred to as FOV position) that is out of the center of an X-ray detector and displaying the set field of view in a magnified state. Specifically, an X-ray diagnostic apparatus sets a field of view by setting an FOV size and then setting an FOV position. Such an X-ray diagnostic apparatus has a function to change the magnifying ratio of a display image by switching the FOV size.

There is no problem when an X-ray diagnostic apparatus as described above is used in normal conditions; however, according to the inventor's consideration, there may be some cases where when the FOV size is switched, the FOV position that was set before is not maintained. For example, it is assumed that in an X-ray diagnostic apparatus, a field of view is set at an FOV position which is out of the center of an X-ray detector, and a magnified image having a narrow field of view is presently displayed. At that time, if the FOV size is switched to an entire image of a wide field of view, an entire image having a field of view that is set at the center of the X-ray detector as an FOV position is displayed. If the FOV size is switched to a magnified image again during the entire image being displayed, a magnified image with the center of the entire image set as an FOV position is displayed. In this way, there may be some cases where the FOV position that was set before is not maintained when the FOV size is switched.

BRIEF DESCRIPTION OF THE DRAWINGS

FIG. 1 is a block diagram showing one example of the configuration of an X-ray diagnostic apparatus according to a first embodiment.

FIG. 2 is a diagram showing one example of the configuration of diaphragm blades in the first configuration.

FIG. 3 is a diagram exemplarily showing a method of moving diaphragm blades when all the diaphragm blades in the first embodiment are respectively independently movable.

FIG. 4A is a diagram exemplarily showing a method of moving diaphragm blades when the movement of the diaphragm blades in the first embodiment is restricted.

FIG. 4B is another diagram exemplarily showing the method of moving diaphragm blades when the movement of the diaphragm blades in the first embodiment is restricted.

FIG. 8B is a diagram showing a display example of a display image corresponding to the medium field of view M2a shown in FIG. 7B.

FIG. 8C is a diagram showing a display example of a display image corresponding to the narrow field of view M3 shown in FIG. 7C.

FIG. 9A is a diagram exemplarily showing the positional relationship between the normal field of view N0 and the narrow field of view M3 in a second specific example of the first embodiment.

FIG. 9B is a diagram exemplarily showing the positional relationship between narrow fields of view M3 and M3a before and after a movement in the second specific example.

FIG. 9C is a diagram exemplarily showing the positional relationship between the narrow field of view M3 and the medium field of view M2 in the second specific example.

FIG. 10A is a diagram showing a display example of a display image corresponding to the narrow field of view M3 shown in FIG. 9A.

FIG. 10B is a diagram showing a display example of a display image corresponding to the medium field of view M2 shown in FIG. 9A.

FIG. 11A is a diagram showing another display example of a display image corresponding to the medium field of view M2 shown in FIG. 7A.

FIG. 11B is a diagram showing still another display example of a display image corresponding to the medium field of view M3 shown in FIG. 7C.

FIG. 13A is a schematic diagram for illustrating a storage circuitry in the second embodiment.

FIG. 13B is another schematic diagram for illustrating the storage circuitry in the second embodiment.

FIG. 13C is still another schematic diagram for illustrating the storage circuitry in the second embodiment.

FIG. 15 is a diagram for illustrating the operations of the control circuitry in the second embodiment.

FIG. 18 is a diagram for illustrating the operations of the control circuitry in the third embodiment.

FIG. 19 is a diagram exemplarily showing a reference image according to a fourth embodiment.

FIG. 20 is a diagram exemplarily showing a display window in the fourth embodiment.

FIG. 22 is a block diagram showing one example of the configuration of an X-ray diagnostic apparatus according to a fifth embodiment.

DETAILED DESCRIPTION

Figure 5:
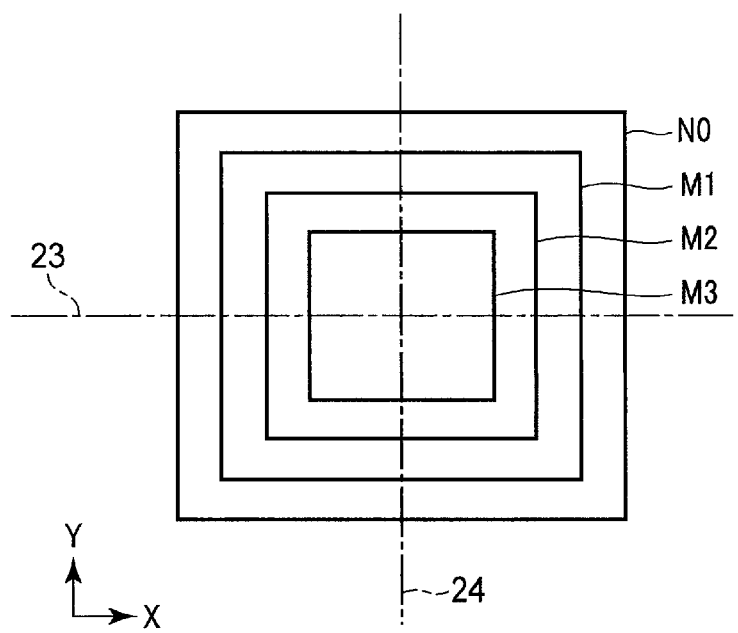
FIG. 5 is a diagram showing one example of a plurality of FOV sizes in the first embodiment.

According to one embodiment, an X-ray diagnostic apparatus includes an X-ray movable diaphragm and processing circuitry. The X-ray movable diaphragm limits an irradiation field of an X-ray. The processing circuitry sets an FOV size related to the irradiation field, sets a virtual field of view having the FOV size, the virtual field of view being able to include an outside region of an X-ray detection region and at least a part of the X-ray detection region, and controls the X-ray movable diaphragm so as to apply the X-ray to a common region between the virtual field of view and the X-ray detection region.

An object to be achieved is to provide an X-ray diagnostic apparatus capable of positioning a region of interest in the center of a display image even when X-ray is applied to the end of an X-ray detection region.

According to one embodiment, an X-ray diagnostic apparatus includes an X-ray tube, an X-ray movable diaphragm, an X-ray detector, a memory and processing circuitry. The X-ray tube generates X-ray. The X-ray movable diaphragm limits an irradiation field of the generated X-ray. The X-ray detector having an X-ray detection region to detect the X-ray. The memory stores an FOV size in association with an FOV position, the FOV size being related to the irradiation field, the FOV position being within the X-ray detection region. The processing circuitry set the FOV size, reads out, from the memory, the FOV position associated with the set FOV size to control the X-ray movable diaphragm, based on the FOV size and the FOV position.

Another object to be achieved is to provide an X-ray diagnostic apparatus capable of maintaining, when the FOV size is switched, an FOV position that was set before. The same holds true for the third embodiment and the fourth embodiment.

According to one embodiment, an X-ray diagnostic apparatus includes an X-ray tube, an X-ray movable diaphragm, an X-ray detector, a memory and processing circuitry. The X-ray tube generates X-ray. The X-ray movable diaphragm limits an irradiation field of the generated X-ray. The X-ray detector having an X-ray detection region to detect the X-ray. The memory stores an FOV size in association with an FOV position, the FOV size being related to the irradiation field, the FOV position being within the X-ray detection region. The processing circuitry sets the FOV size related to the irradiation field, sets a virtual field of view having the first FOV size, the virtual field of view being able to include an outside region of an X-ray detection region and at least a part of the X-ray detection region, controls the X-ray movable diaphragm so as to apply the X-ray to a common region between the virtual field of view and the X-ray detection region, sets a second FOV size different from the first FOV size, and reads out, from the memory, an another FOV position associated with the set second FOV size to control the X-ray movable diaphragm, based on the second FOV size and the another FOV position associated with the set second FOV size.

A further object to be achieved is to provide an X-ray diagnostic apparatus capable of positioning a region of interest in the center of a display screen even when X-ray is applied to the end of an X-ray detection region, and further capable of maintaining, when the FOV size is switched, an FOV position that was set before.

Hereinafter, each of the embodiments will be explained with reference to the drawings. The same elements as or similar elements to those that have been explained are provided with the same reference signs as or similar reference signs to those of the explained elements, and overlapping descriptions will be omitted, and elements not previously explained will be mainly explained.

First Embodiment

FIG. 1 is a block diagram showing a configuration example of an X-ray diagnostic apparatus 1 according to a first embodiment. The X-ray diagnostic apparatus 1 includes an X-ray high-voltage generator 2, an X-ray source device 3, an X-ray detector 4, a support frame 5, a bed having a table top 6, an image generation circuitry 7, a communication interface circuitry 8, an input interface circuitry 9, a control circuitry 10, a processing circuitry 11, a storage circuitry 12, and a display circuitry 13. The X-ray source device 3 includes an X-ray tube 3a and an X-ray movable diaphragm 3b. The X-ray diagnostic apparatus 1 corresponds to an X-ray fluoroscopic diagnosis apparatus, for example, for use in digestive tract angiographic examinations, etc. The X-ray diagnostic apparatus 1 may be an X-ray fluoroscopic diagnosis apparatus for circulatory organs, for example, for use in angiographic examinations.

The X-ray high-voltage generator 2 generates a tube current to be supplied to the X-ray tube 3a and a tube voltage to be applied to the X-ray tube 3a. The X-ray high-voltage generator 2 supplies, to the X-ray tube 3a, tube currents suitable for the X-ray imaging and for the X-ray fluoroscopy, and applies, to the X-ray tube 3a, tube voltages suitable for the X-ray imaging and for the X-ray fluoroscopy, under the control of the control circuitry 10. The X-ray high-voltage generator 2 corresponds, for example, to a high-voltage generator based on an inverter control method.

The X-ray tube 3a generates X-ray based on the tube current supplied from the X-ray high-voltage generator 2 and the tube voltage applied from the X-ray high-voltage generator 2. The X-ray generated by the X-ray tube 3a is applied to a subject P. The X-ray tube 3a corresponds, for example, to a rotating anode type X-ray tube. Also, the X-ray tube 3a may be, for example, a fixed anode X-ray tube, etc.

Hereinafter, a central axis along which X-ray is applied is denoted by a Z-axis. An axis that is perpendicular to the Z-axis and is in a longitudinal direction of the table top 6 is denoted by a Y-axis, and an axis perpendicular to the Z-axis and the Y-axis is denoted by an X-axis.

The X-ray movable diaphragm 3b limits the irradiation field of the X-ray generated by the X-ray tube 3a. The X-ray movable diaphragm 3b can apply X-ray only to an imaging region (or imaging range) of a subject P desired by the operator, by limiting the irradiation field of the X-ray. That is, the X-ray movable diaphragm 3b can prevent a region (or a range) different from the imaging region (or imaging range) from being subjected to unnecessary exposure. Also, the X-ray movable diaphragm 3b can reduce scattered X-ray and remove off-focus X-ray. Hereinafter, the wording, "limiting the irradiation field of X-ray" may be mutually referred to as the wording, "shielding X-ray" and "limiting down X-ray".

The X-ray movable diaphragm 3b has, for example, a beam-limiting mechanism 20 as illustrated in FIG. 2. The beam-limiting function includes, for example, diaphragm blades 21a and 21b that limit X-ray diffusing in the X-axis direction, and diaphragm blades 22a and 22b that limit X-ray diffusing in the Y-axis direction. Hereinafter, the range enclosed by the diaphragm blades 21a, 21b, 22a, and 22b is regarded as an irradiation field of X-ray. Note that the beam-limiting mechanism 20 in FIG. 20 shows a simplified diaphragm mechanism, and it may be designed to have a multilayered structure by arranging a plurality of beam-limiting mechanisms 20. It is based on the assumption that X-ray is not applied to portions other than the irradiation field.

Herein, a method of limiting X-ray to a region of interest (ROI) by the diaphragm blades 21a, 21b, 22a, and 22b will be described. Hereinafter, the positions of the diaphragm blades 21a, 21b, 22a, and 22b illustrated in FIG. 2 are defined as initial positions. With respect to the initial positions, it is assumed that an intersection point between a first central axis 23 and a second central axis 24 resides at the center of the irradiation field of the X-ray. It is also assumed that the irradiation field is already limited to a certain degree in the positions of the diaphragm blades shown in FIG. 2, and there is no unnecessary exposure.

FIG. 3 illustrates a method of moving diaphragm blades in a case where the diaphragm blades 21a, 21b, 22a, and 22b are respectively independently movable. The diaphragm blade 21a is movable along a moving direction xl which is an X-axis direction with the initial position set as a reference. The diaphragm blade 22b is movable along a moving direction yl which is a Y-axis direction with the initial position set as a reference. At that time, the beam-limiting mechanism 20 can limit the X-ray to a region of interest (ROI) by moving only the diaphragm blades 21a and 22b. Therefore, the diaphragm blades 21b and 22a are maintained as they are in the initial positions without moving.

FIG. 4A and FIG. 4B illustrate a method of moving diaphragm blades in a case where there is a limitation on the movement of the diaphragm blades. In FIG. 4A and FIG. 4B, the diaphragm blade 21a and the diaphragm blade 21b move in conjunction with each other, and the diaphragm blade 22a and the diaphragm blade 22b move in conjunction with each other. Namely, two pairs of diaphragm blades can move left-right symmetrically and up-down symmetrically.

Initially, the beam-limiting mechanism 20 moves along the moving directions x and y so that the region of interest (ROI) is positioned at the center of the irradiation field. Thereafter, the diaphragm blades 21a and 21b are movable respectively along the moving directions x2a and x2b. Simultaneously, the diaphragm blades 22a and 22b are movable respectively along the moving directions y2a and y2b. By configuring the diaphragm blades to be movable in the way described above, the X-ray can be limited to the region of interest (ROI).

The X-ray detector 4 detects X-ray that has been generated from the X-ray tube 3a and has transmitted through a subject P. The X-ray detector 4 includes a flat panel detector (FPD) capable of detecting X-ray. The FPD includes a plurality of semiconductor detection elements. As semiconductor detection elements, there are an indirect conversion form and a direct conversion form. The indirect conversion form is a form of converting emitted X-ray into light by a scintillator such as a fluorescent substance and converting the converted light into an electric signal. The direct conversion form is a form of directly converting emitted X-ray into an electric signal. An image intensifier may be adopted for the X-ray detector 4. In this specification, the X-ray detectable range or a range in which X-ray is detected, in the X-ray detector 4, is referred to as "X-ray detection region".

Electrical signals generated by a plurality of semiconductor detection elements along with the emission of X-ray are output to an unillustrated Analog-to-Digital converter (A/D converter). The A/D converter converts electric signals into digital data. The A/D converter outputs the digital data to the image generation circuitry 7.

FIG. 5 illustrates a relationship between an X-ray detection region and a plurality of irradiation fields. In this specification, for example, fields of view of four types of FOV size are defined, in descending order of irradiation field: Normal field of view N0, wide field of view M1, medium field of view M2, and narrow field of view M3. The normal field of view N0 relates, for example, to an irradiation field in which X-ray can be detected from the entire surface of an X-ray detection region. The wide field of view M1 relates to an irradiation field narrower than the irradiation field of the normal field of view NO. The medium field of view M2 relates to an irradiation field narrower than the irradiation field of the wide field of view M1. The narrow field of view M3 relates to an irradiation field narrower than the irradiation field of the medium field of view M2. Since the FOV sizes are associated with the size of the irradiation field, "the FOV size widens" also means "the irradiation field widens".

An X-ray image corresponding to each of the FOV sizes is displayed to fit with a display window of a later-mentioned display (for example, in a magnified state). Specifically, a display based on the wide field of view M1 is displayed to be magnified as compared to the display based on the normal field of view N0. Therefore, switching the FOV size is synonymous with switching the magnification ratio of an image displayed on a display window. If the respective fields of view N0 to M3 are arranged in descending order of magnification ratio, it results in M3, M2, M1, and N0.

The support frame 5 movably supports the X-ray source device 3 and the X-ray detector 4 that are placed opposite to one another. Specifically, the support frame 5 corresponds to a frame of over-tube type where the X-ray source device 3 is upwardly disposed with respect to the surface of the table top 6. As the support frame 5, a frame of an under tube type where the X-ray source device 3 is downwardly disposed with respect to the surface of the table top 6 may be adopted. Also, as the support frame 5, a structure based on a C arm or an Q-arm may be adopted. Furthermore, as the support frame 5, a structure using two arms (e.g., robot arms, etc.) independently supporting each of the X-ray source device 3 and the X-ray detector 4 may be adopted.

A bed not illustrated in the figure includes a table top (also referred to as a spine table) on which a subject P is placed.

An unillustrated drive device drives the support frame 5 and the bed, respectively, for example, by the control of the control circuitry 10. During X-ray fluoroscopy and during X-ray photography, a subject P placed on the table top 6 is placed between the X-ray source device 3 and the X-ray detector 4. Also, the drive device drives the X-ray diaphragm 3b, for example, by the control of the control circuitry 10. The drive device may rotate the X-ray detector 4 with respect to the X-ray source device 3, under the control of the control circuitry 10.

The image generation circuitry 7 generates an X-ray image, based on digital data output from the X-ray detector 4 via the A/D converter. The image generation circuitry 7 outputs the generated X-ray image to the processing circuitry 11, the storage circuitry 12, an unillustrated external storage device, etc.

The communication interface circuitry 8 is a circuitry relating to, for example, a network, and the unillustrated external storage device. An X-ray image, etc. obtained by the X-ray diagnostic apparatus 1 can be transferred to other devices via the communication interface circuitry 8 and a network. Hereinafter, when information is exchanged via the communication interface circuitry 8, the description, "via the communication interface circuitry 8" is omitted.

The input interface circuitry 9 inputs X-ray irradiation conditions, such as imaging conditions for X-ray imaging and fluoroscopic conditions for X-ray fluoroscopy, desired by the operator; a fluoroscopy/imaging position; an irradiation field; and a region of interest (ROT) in an X-ray image, etc. in response to operator's instructions. Specifically, the input interface circuitry 9 relays various instructions, commands, information, selection, and settings from the operator into the X-ray diagnostic apparatus 1.

The input interface circuitry 9 is implemented by a joystick for performing settings of a region of interest, etc., a track ball, a switch button, a mouse, a keyboard, a touch pad for performing input operations by touching an operation surface, a touch panel display in which a display screen is integrated with a touch pad, a foot switch for imaging, and a microphone for sound recognition, etc. The input interface circuitry 9 is connected to the control circuitry 10 and an electric signal to output it to the control circuitry 10.

In this specification, the input interface circuitry 9 is not limited to the one that includes physical operation components such as a mouse and a keyboard. For example, an electric signal processing circuitry that receives an electric signal corresponding to an input operation from an external input device provided separately from the X-ray diagnostic apparatus and outputs this electric signal to the control circuitry 10 is also encompassed in examples of the input interface circuitry 9.

The control circuitry 10 is a processor to control, for example, various circuitries and a drive device in the X-ray diagnostic apparatus 1. The control circuitry 10 temporarily stores, in an unillustrated memory, information such as operator's instructions input from the input interface circuitry 9. The control circuitry 10 controls the X-ray high-voltage generator 2, the X-ray movable diaphragm 3b, and the drive device, etc. to implement X-ray imaging and X-ray fluoroscopy in accordance with operator's instructions stored in the memory. Also, the control circuitry 10 controls X-ray image generation processing in the image generation circuitry 7, and image generation processing in the processing circuitry 11, etc.

Furthermore, the control circuitry 10 executes various functions for performing settings and control relating to the X-ray diaphragm in accordance with operator's instructions stored in the memory. Examples of the various functions include an FOV size setting function 10a, a virtual field of view setting function 10b, a beam-limiting position calculation function 10c, and a diaphragm control function 10d, etc.

The FOV size setting function 10a sets an FOV size relating to the irradiation field of X-ray by operator's operations. At that time, the operator selects a discretional FOV size (or a discretional magnification ratio), for example, by pressing down a switch button of the input interface circuitry 9. In other words, the FOV size setting function 10a sets an FOV size relating to the irradiation field of X-ray to any of a plurality of preliminarily prepared FOV sizes by operator's operations. As a method of inputting the FOV size, a method of selecting an FOV size by touching a touch panel, and a method of selecting an FOV size by means of sound recognition may be used.

The virtual field of view setting function 10b sets a virtual field of view by operator's operations. Herein, a "virtual field of view" is a field of view that can include an outer side of an X-ray detection region that was not assumed in the past and does not match an irradiation range within which X-ray is actually applied. The "virtual field of view" is synonymous with an image to be displayed on the later-described display. Specifically, the virtual field of view setting function 10b sets, for example, a virtual field of view having an FOV size set by the FOV size setting function 10a so as to be able to run over from the X-ray detection region of the X-ray detector 4. Herein, "sets a virtual field of view" may be referred to as "sets an FOV position of a virtual field of view". The virtual field of view setting function 10b sets an FOV position of the virtual field of view so as to position a region of interest at the center of the virtual field of view, ignoring the positional relationship between a virtual field of view corresponding to the FOV size set by the FOV size setting function 10a and the X-ray detection region of the X-ray detector 4. For the positional relationship, there are two positional relationships. For example, a positional relationship in a case where the virtual field of view is present in a position of a region including an outer side region of the X-ray detection region, and a positional relationship in a case where the virtual field of view is present in a position that does not include the outer side of the X-ray detection region. The former positional relationship corresponds to a case where the virtual field of view runs over from the X-ray detection region, and the latter positional relationship corresponds to a case where the virtual field of view does not run over from the X-ray detection region. "To position a region of interest at the center of the virtual field of view, ignoring the positional relationship" means putting a region of interest in the center of a virtual field of view, in both cases of the two positional relationships. Conventionally, since "the positional relationship between a field of view and an X-ray detection region" is not ignored, the field of view never includes the outer side region of the X-ray detection region. Of the two positional relationships, "to position a region of interest at the center of the virtual field of view, ignoring the positional relationship" may be referred to as "to position a region of interest at the center of the virtual field of view also in the case where the virtual field of view includes the outer side region of the X-ray detection region". In this process, the operator moves the virtual field of view to a desired position by operating, for example, the joystick of the input interface circuitry 9. The FOV position is a discretional position that the center of a virtual field of view falls within the X-ray detection region.

The virtual field of view setting function 10$b$ may set a virtual field of view (or an FOV position of a virtual field of view), taking switching of a plurality of FOV sizes as a trigger. Also, the virtual field of view setting function 10$b$ may set a virtual field of view (or an FOV position of a virtual field of view) so that the center of the virtual field of view is positioned within the X-ray detection region.

The beam-limiting position calculation function 10$c$ calculates a beam-limiting position corresponding to the virtual field of view (or a virtual field of view at the FOV position) set by the FOV size setting function 10$a$ and the virtual field of view setting function 10$b$.

The diaphragm control function 10$d$ controls the X-ray movable diaphragm 3$b$ based on the set virtual field of view. At that time, the diaphragm control function 10$d$ controls the X-ray movable diaphragm 3$b$ so as to apply X-ray to a common region between the set virtual field of view and the X-ray detection region. In other words, the diaphragm control function 10$d$ controls the X-ray movable diaphragm 3$b$ based on the virtual field of view at the set FOV position (or a calculated beam-limiting position). At that time, if the virtual field of view at the set FOV position includes an outer side region of the X-ray detection region, the diaphragm control function 10$d$ further controls the X-ray movable diaphragm 3$b$ so as not to apply the X-ray to the outer side region of the X-ray detection region.

The processing circuitry 11 includes, as hardware resources, a processor and a memory. The processing circuitry 11 reads out a control program stored in the storage circuitry 12 in response to an instruction for starting which is input by the operator via the input interface circuitry 9. The processing circuitry 11 executes various functions relating to image processing for displaying, on the display, X-ray images generated by the image generation circuitry 7, in accordance with the control program readout. Examples of the various functions include an image cut-out position calculation function 11$a$, an image cut-out function 11$b$, an image processing function 11$c$, and an image magnification function 11$d$, etc.

The image cut-out position calculation function 11$a$ calculates, as an image cut-out position, a range of the X-ray applied to the X-ray detection region of the X-ray detector 4, based on the beam-limiting position calculated in the beam-limiting position calculation function 10$c$, the position of the X-ray source device 3, and the position of the X-ray detector 4.

The image cut-out function 11$b$ cuts out an X-ray image, based on the image cut-out position.

The image processing function 11$c$ generates a processed image (display image) including the cut-out X-ray image that was cut out in the image cut-out function lib. Specifically, the image processing function 11$c$ performs processing, on an X-ray image, to complement an image showing the outer side region of the X-ray detection region (padding image). If the virtual field of view does not include the outer side region of the X-ray detection region, the processing by the image processing function 11$c$ is omitted.

Herein, the padding image is an image for filling a blank between a display image corresponding to a virtual field of view and an X-ray image corresponding to part of the virtual field of view and is an image different in pattern from the X-ray image. Also, the padding image is an image that is not influenced by an examination result of a subject. As a padding image, for example, a mesh image of black-and-white bi-level may be used, and if a padding image is displayed on a color display, hue information may be used. A mesh image is one example in a case where the padding image has a pattern, and the mesh image may be changed into an image with parallel lines or a pattern image with a plurality of lines (straight lines or curves), such as substantially randomly crossing lines. Similarly, the mesh image may be changed into a pattern image in which graphic symbols, symbols, or characters are nearly uniformly or nearly randomly scattered. The mesh image is not limited thereto, and it may be changed into a unicolor image whose entire surface is white or black, or other discretional picture images. Also, the padding image may include, in part, memorandum information, such as character strings relating to a subject or an examination, etc. The padding image may be distinguished from an X-ray image by the form indicating the outline of the padding image using a frame, not limited to the case where the padding image is distinguished from an X-ray image by the in-plane form, such as the above-described white-black 2-gradation pattern image or hue information. Alternatively, the padding image may be made into a form where an in-plane form is combined with a form indicating the outline.

The image magnification function 11$d$ magnifies a processed image processed in the image processing function 11$c$ or a non-processed X-ray image to fit with a display window of a display 30.

The storage circuitry 12 is composed of memories for recording electric information, such as a hard disk drive (HDD), and peripheral circuitries such as a memory controller, and a memory interface accompanied by the memories. The memories are not limited to a HDD, and as the memories, a solid state drive (SSD), magnetic disk (e.g., Floppy Disk™ and hard disk), an optical disk (CD, DVD, Blu-Ray™, etc.), and a semiconductor memory can be suitably used.

The storage circuitry 12 stores data constellation of various types of data, such as various X-ray images generated by the image generation circuitry 7, X-ray images processed by the processing circuitry 11, a system control program of the X-ray diagnostic apparatus 1, a diagnosis protocol executed in the control circuitry 10, operator's instructions transmitted from the input interface circuitry 9, imaging conditions relating to X-ray imaging and fluoroscopy conditions relating to fluoroscopy; error information; and various types of data received through the network.

The display circuitry 13 is composed of a display for displaying medical images, an internal circuitry for supplying a display signal to the display, and peripheral circuitries, such as a connector or a cable that connects the display and the internal circuitry.

The display displays X-ray images generated by the image generation circuitry or display images processed by the processing circuitry 11. As for the display, the entire surface of the display may be used as a display window for displaying X-ray images, or part of the display may be used as a display window, or the display may be configured to switch between the entire surface thereof and part of the entire surface thereof. Also, the display may be configured to display input screens relating to inputs of fluoroscopy/imaging positions, X-ray irradiation conditions, etc. Also, the display may display, for example, an X-ray image and input screens, in parallel.

Figure 6:
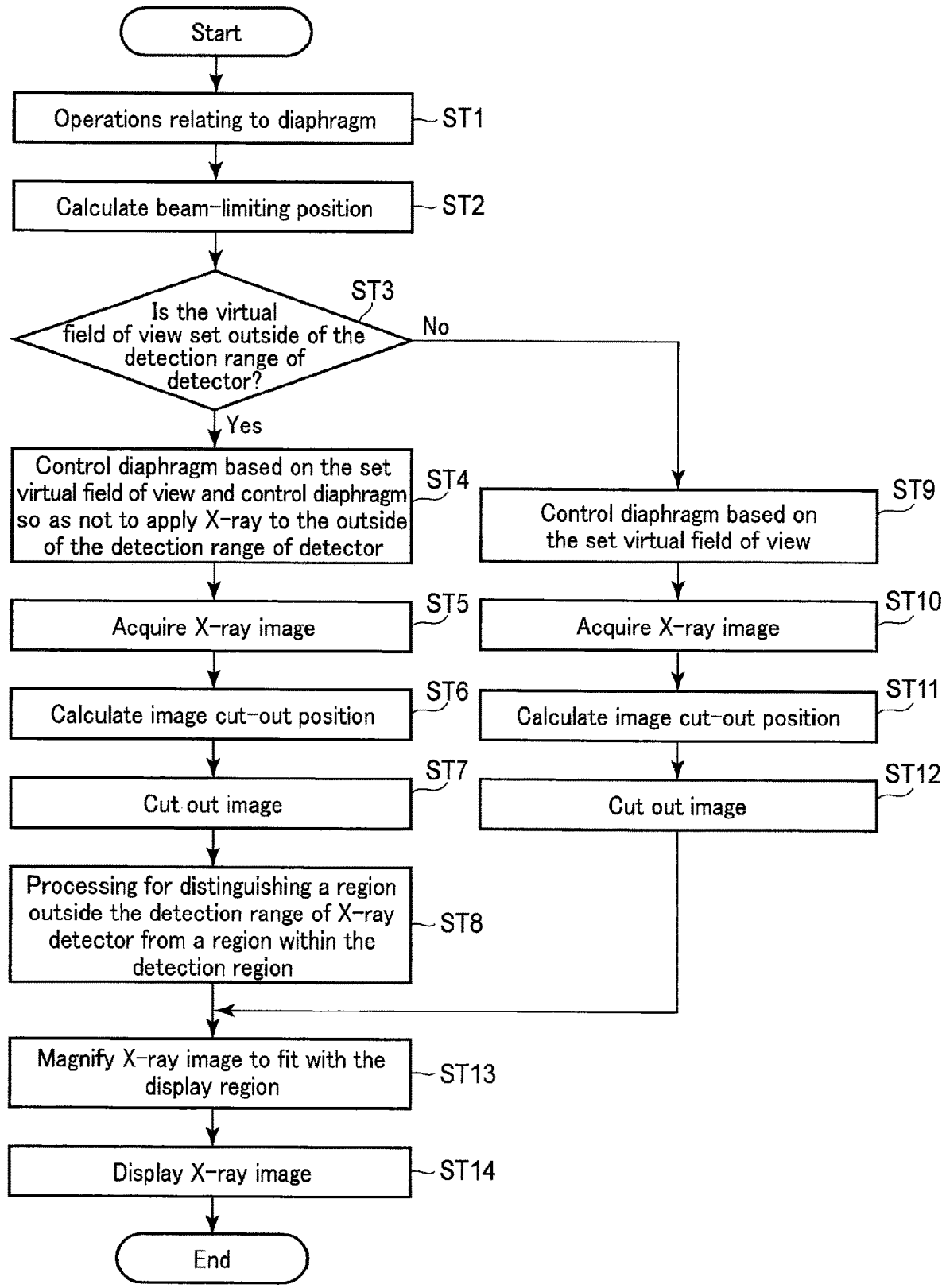
FIG. 6 is a flowchart showing one example of the movement of the X-ray diagnostic apparatus according to the first embodiment.

Next, the operations of the X-ray diagnostic apparatus 1 configured as above will be described using the flowchart shown in FIG. 6. The following are mainly explanations on settings and control relating to the X-ray diaphragm by means of the control circuitry 10, and the image generation processing by the processing circuitry 11.

First, a subject P is placed on the table top 6 of the bed. In the X-ray diagnostic apparatus 1, a preset examination type and a preset examination name are selected, and imaging conditions associated with the selected examination type and examination name are set, by operator's operations. Thereafter, the X-ray diagnostic apparatus 1 starts X-ray fluoroscopy by operator's operations and starts step ST1.

In step ST1, the X-ray diagnostic apparatus 1 accepts an operation relating to beam-limiting. Specifically, the FOV size setting function 10a sets any one of a plurality of fields of view by operator's instructions. The setting of an FOV size may be referred to as switching of FOV sizes. In either case, at that time, the operator selects a discretional FOV size (or a discretional magnification ratio) by pressing down a switch button of the input interface circuitry 9, for example. The virtual field of view setting function 10b sets a virtual field of view (or an FOV position), taking the setting of an FOV size, as a trigger.

The configuration of the virtual field of view setting function 10b is not limited thereto, and the virtual field of view setting function 10b may be configured to set a virtual field of view (or an FOV position) by operator's instructions, as long as the FOV size has been already set. At that time, the operator moves the center of the virtual field of view to the position of a desired region of interest, for example, by operating a joystick of the input interface circuitry 9. Before and after the movement, the virtual field of view (or the FOV position) is set so that the center of the virtual field of view is present within the X-ray detection region of the X-ray detector 4.

The FOV size and the virtual field of view (or the FOV position) may be set substantially simultaneously by using a reference image, for example. For the reference image, an X-ray image (or an X-ray fluoroscopic image) having a normal field of view may be used, and a tentative image that can be radiographed with a normal field of view may be used. If a reference image is preliminarily obtained, X-ray fluoroscopy may be temporarily stopped.

In step ST2, the beam-limiting position calculation function 10c calculates a beam-limiting position corresponding to the virtual field of view (or a virtual field of view at the FOV position) set in step ST1.

In step ST3, the control circuitry 10 determines whether or not the virtual field of view is set in the outer side of the X-ray detection region of the detector. Specifically, the control circuitry 10 determines whether or not the beam-limiting position calculated in step ST2 includes the outside of the detection range of the X-ray detector 4. If the beam-limiting position includes the outside of the detection range of the X-ray detector 4, the process proceeds to ST4, and if this is not the case, the process proceeds to step ST9.

In step ST4, the diaphragm control function 10d controls the X-ray movable diaphragm 3b, based on the set virtual field of view (or a field of view at the FOV position, or the calculated beam-limiting position), and so as not to apply X-ray to the outside of the detection range of the X-ray detector 4.

In step ST5, the processing circuitry 11 acquires an X-ray image generated by the image generation circuitry 7.

In step ST6, the image cut-out position calculation function 11a calculates, as an image cut-out position, a range in which the X-ray is applied to the X-ray detection region of the X-ray detector 4, based on the beam-limiting position calculated in step ST2, the position of the X-ray source device 3, and the position of the X-ray detector 4.

In step ST7, the image cut-out function lib cuts out an X-ray image, based on the image cut-out position calculated in step ST6.

In step ST8, the image processing function 11c generates a processed image corresponding to the virtual field of view at the set FOV position and including an X-ray image cut out in step ST7. Specifically, the image processing function 11c performs processing, on the X-ray image, to complement a padding image indicating the outer side region of the X-ray detection region. With this, the image processing function 11c generates a processed image (display image) corresponding to the field of view so that the X-ray image and the padding image are connected together. The padding image in the processed image may be generated as a white-black 2-gradation mesh image, and may be generated as a color image using hue information.

In step ST9, the diaphragm control function 10d controls the X-ray movable diaphragm 3b, based on the virtual field of view at the set FOV position (or the calculated beam-limiting position).

In step ST10, the processing circuitry 11 acquires the X-ray image generated by the image generation circuitry 7.

In step ST11, the image cut-out position calculation function 11a calculates, as an image cut-out position, a range in which the X-ray is applied to the X-ray detection region of the X-ray detector 4, based on the beam-limiting position calculated in step ST2, the position of the X-ray source device 3, and the position of the X-ray detector 4.

In step ST12, the image cut-out function 11b cuts out an X-ray image, based on the image cut-out position calculated in step ST6.

In step ST13, the image magnification function 11d magnifies the processed image generated in step ST8 or the X-ray image cut out in step ST12 so as to fit with the display window of the display.

In step ST14, the display circuitry 13 displays the processed image or X-ray image magnified in step ST13.

Next, specific examples of the above-mentioned operations will be described with reference to FIGS. 7A to 7C, FIGS. 8A to 8C, FIGS. 9A to 9C, FIGS. 10A to 10B, and FIGS. 11A to 11B. In these specific examples, settings of FOV sizes and FOV positions are mainly described, and explanations on the image processing by the processing circuitry 11 are omitted.

First Specific Example

Figure 7A:
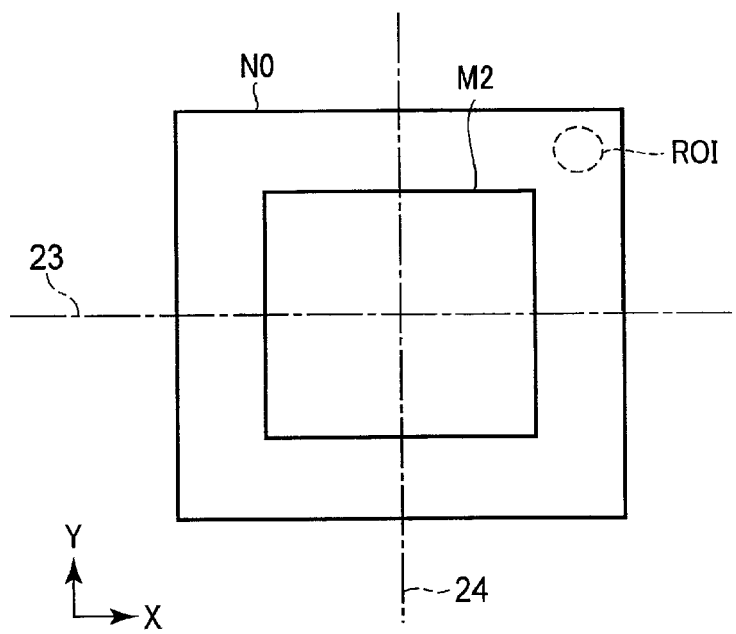
FIG. 7A is a diagram exemplarily showing the positional relationship between a normal field of view N0 and a medium field of view M2 in a first specific example of the first embodiment.
Figure 7B:
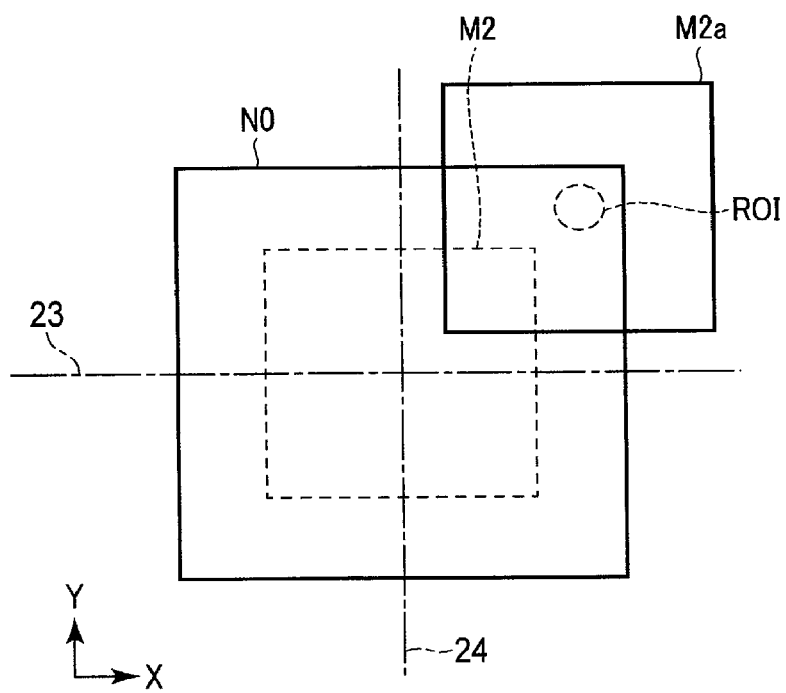
FIG. 7B is a diagram exemplarily showing the positional relationship between medium fields of view M2 and M2a before and after a movement in the first specific example.
Figure 7C:
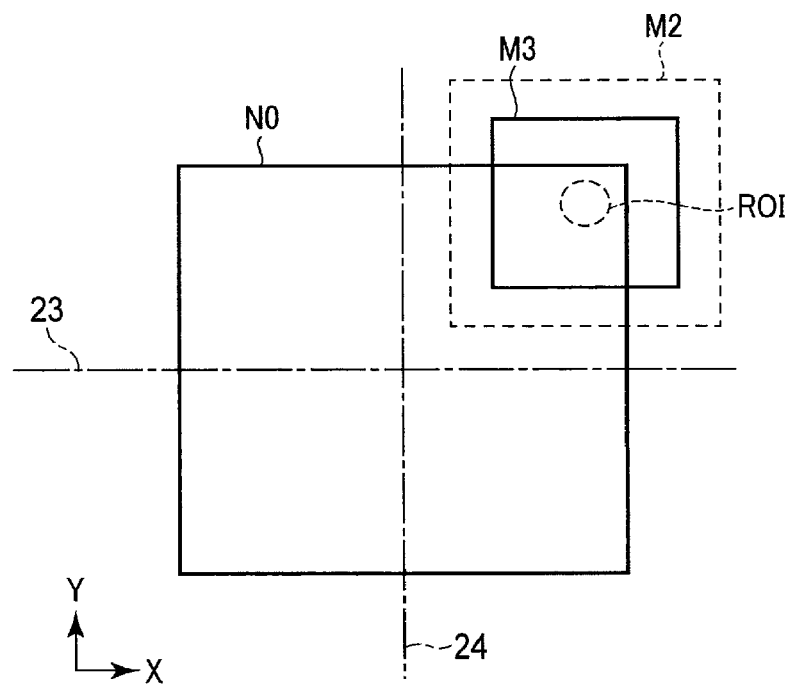
FIG. 7C is a diagram exemplarily showing the positional relationship between the medium field of view M2 and a narrow field of view M3 in the first specific example.
Figure 8A:
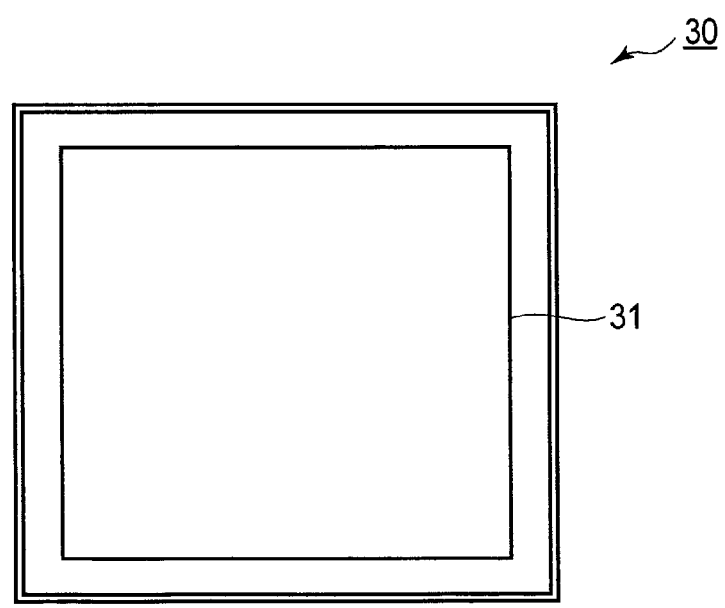
FIG. 8A is a diagram showing a display example of a display image corresponding to the medium field of view M2 shown in FIG. 7A.

A first specific example shows a series of operations, in which switching from a normal field of view N0 to a medium field of view M2 is performed by operator's operations (FIG. 7A), the medium field of view M2 is moved (FIG. 7B), and switching from the medium field of view M2 to a narrow field of view M3 is performed (FIG. 7C). In this specific example, when the medium field of view M2 is moved, the field of view is set at an FOV position (a position of a field of view) including the outer side of an X-ray detection region. To facilitate understanding, a normal field of view N0 corresponding to the X-ray detection region is shown in FIGS. 7A to 7C.

FIG. 7A is a diagraph illustrating the positional relationship between the normal field of view N0 and the medium field of view M2 in a case where the irradiation field is narrowed from the normal field of view N0 to the medium field of view M2. The operator selects an FOV size of the medium field of view M2, for example, by pressing down a switch button of the input interface circuitry 9. The FOV size setting function 10a sets an FOV size of the medium field of view M2 by operator's operations. At that time, as illustrated in FIG. BA, an X-ray image obtained from the irradiation field of the medium field of view M2 is displayed on a display window 31 of a display 30.

FIG. 7B is a diagram illustrating the positional relationship between the medium field of view M2 before a movement and the medium field of view M2a after the movement in a case where the medium field of view M2 (M2 before moved) shown in FIG. 7A is moved. The operator moves the medium field of view M2 so that a region of interest is positioned at the center of a virtual field of view, for example, by operating a joystick of the input interface circuitry 9. The virtual field of view setting function 10b sets the medium field of view M2a so that the region of interest is positioned at the center of a virtual field of view by operator's operations. At that time, the medium field of view M2a after the movement includes an outer side region of the X-ray detection region. Therefore, as illustrated in FIG. 8B, a mesh image 33 representing the outer side region of the X-ray detection region is displayed along with the X-ray image on a display window 32.

FIG. 7C is a diagram illustrating the positional relationship between a medium field of view M2 and a narrow field of view M3 in a case where the irradiation field is narrowed from the medium field of view M2 to the narrow field of view M3. The operator selects an FOV size of the narrow field of view M3, for example, by pressing down a switch of the input interface circuitry 9. The FOV size setting function 10a sets an FOV size of the narrow field of view M3 by operator's operations. At that time, the narrow field of view M3 includes an outer side region of the X-ray detection region. Therefore, as illustrated in FIG. 8C, a mesh image 35 representing the outer side region of the X-ray detection region is displayed along with the X-ray image on a display window 34.

Second Specific Example

A second specific example shows a series of operations, in which switching from a normal field of view N0 to a narrow field of view M3 is performed by operator's operations (FIG. 9A), the narrow field of view M3 is moved (FIG. 9B), and switching from the narrow field of view M3 to a medium field of view M2 is performed (FIG. 9C). This specific example is configured so that in the switching from the narrow field of view M3 to the medium field of view M2, the outer side region of the X-ray detection region is included in the virtual field of view. To facilitate understanding, a normal field of view N0 corresponding to the X-ray detection region is shown in FIGS. 9A to 9C.

FIG. 9A is a diagram illustrating the positional relationship between a normal field of view N0 and a narrow field of view M3 in a case where the irradiation field is narrowed from the normal field of view N0 to the narrow field of view M3. The operator selects an FOV size of the narrow field of view M3, for example, by pressing down a switch button of the input interface circuitry 9. The FOV size setting function 10a sets an FOV size of the narrow field of view M3 by operator's operations. At that time, as illustrated in FIG. 10A, an X-ray image obtained from the irradiation field of the narrow field of view M3 is displayed on a display window 41 of a display 40.

FIG. 9B is a diagram illustrating the positional relationship between the narrow field of view M3 before being moved and the narrow field of view Mia after the movement in a case where the narrow field of view M3 (M3 before being moved) shown in FIG. 9A is moved. The operator moves the narrow field of view M3 so that a region of interest is positioned at the center of the virtual field of view, for example, by operating the joystick of the input interface circuitry 9. The virtual field of view setting function 10b sets a narrow field of view M3 so that the region of interest is positioned at the center of the virtual field of view. At that time, since the narrow field of view after the movement falls within the X-ray detection region, the display of an X-ray image results in an ordinary display as shown in one example in FIG. 10A.

FIG. 9C is a diagram illustrating the positional relationship between the narrow field of view M3 and the medium field of view M2 in a case where the irradiation field is widened from the narrow field of view M3 to the medium field of view M2. The operator selects an FOV size of the medium field of view M2, for example, by pressing down a switch of the input interface circuitry 9. The FOV size setting function 10a sets the FOV size of the medium field of view M2 by operator's operations. At that time, the medium field of view M2 includes an outer side region of the X-ray detection region. Therefore, as illustrated in FIG. 10B, a mesh image 43 representing the outer side region of the X-ray detection region is displayed along with an X-ray image on a display window 42.

In the above specific examples, the center of a virtual field of view always becomes a center of a display window. As a method of clearly specifying the center of a virtual field of view, there is, for example, a method of displaying a central axis 51 and a central axis 52 as shown in FIGS. 11A and 11B. At this time, the center of the virtual field of view is an intersection point between the central axis 51 and the central axis 52.

FIG. 11A shows a display example in a case where the field of view falls within an X-ray detection region, as in FIG. 7A, etc. If the center of the virtual field of view corresponds to the center of the display window, the outer side portion of the X-ray detection region is not necessarily displayed. For example, FIG. 11B shows a display example in a case where a region of interest is positioned at the end of an X-ray detection region, as in FIG. 7C.

As explained above, according to the first embodiment, the X-ray diagnostic apparatus sets an FOV size related to the irradiation field of X-ray. Also, the X-ray diagnostic apparatus sets a virtual field of view having the FOV size, the virtual field of view being able to include an outside region of an X-ray detection region and at least a part of the X-ray detection region. Also, the X-ray diagnostic apparatus controls the X-ray movable diaphragm so as to apply the X-ray to a common region between the set virtual field of view and the X-ray detection region. Therefore, the X-ray diagnostic apparatus can position a region of interest at the center of a display image even when X-ray is applied to the end of the X-ray detection region, since the X-ray diagnostic apparatus can include the outer side region of the X-ray detection region in the field of view.

According to the first embodiment, the X-ray diagnostic apparatus can set the FOV size to any of a plurality of prepared FOV sizes, and therefore, it can perform magnification and reduction in FOV size at the same magnification ratio, constantly.

According to the first embodiment, the X-ray diagnostic apparatus can set a virtual field of view, taking switching of the plurality of FOV sizes as a trigger, and therefore, it can continuously display a region of interest at the center of a display image, even if an outer side region of the X-ray detection region is included in the field of view at the time of magnifying the FOV size.

According to the first embodiment, the X-ray diagnostic apparatus can prevent erroneous settings of virtual fields of view, since the X-ray diagnostic apparatus sets a virtual field of view so that the center of the virtual field of view is positioned within an X-ray detection region.

According to the first embodiment, the X-ray diagnostic apparatus generates a display image corresponding to a virtual field of view so that an X-ray image is linked to a padding image showing an outer side region of an X-ray detection region. Therefore, the X-ray diagnostic apparatus can continuously display a region of interest at the center of a display image, since the outer side region of the X-ray detection region can be included in a display image corresponding to the virtual field of view. A padding image is an image of a different form from that of the X-ray image. For this reason, the X-ray diagnostic apparatus can distinguish between an X-ray image and a padding image and can display them distinctively.

According to the first embodiment, the X-ray diagnostic apparatus generates the padding image as a mesh image of black-and-white bi-level. Note that an X-ray image is generated as an image representing internal organs and bones of a subject, with multi-gradations between white and black. For this reason, the X-ray diagnostic apparatus can clearly distinguish between X-ray images and padding images and display them distinctively.

Furthermore, according to the first embodiment, the X-ray diagnostic apparatus generates a padding image representing an outer side region of an X-ray detection region by using hue information, and therefore, the X-ray diagnostic apparatus can clearly distinguish between X-ray images and padding images and display them distinctively.

The "processor" mentioned above includes, for example, a central processing unit (CPU), graphics processing unit (GPU), and a circuitry such as an application specific integrated circuitry (ASIC) or programmable logic device (e.g., simple programmable logic device (SPLD), complex programmable logic device (CPLD), and field programmable gate array (FPGA)).

The processor realizes the functions by reading and implementing the programs stored in the storage circuitry 31, which are explained later. Instead of storing the programs in the storage circuitry 31, the programs may be directly loaded in the circuitry of the processor. In such a configuration, the processor reads and implements the programs loaded in the circuitry to realize the various functions.

Each of the processors according to the present embodiment does not always have to be configured as a single circuitry, but a single processor may be provided by combining a plurality of independent circuitries to realize their functions. In addition, a plurality of structural components may be incorporated into one processor to realize their functions. For example, the processor of the control circuitry 10 and the processor of the processing circuitry 11 may be integrated into one processor. Furthermore, the processor of the image generation circuitry 7, the processor of the control circuitry 10, and the processor of the processing circuitry 11 may be integrated into one processor.

Second Embodiment

Figure 12:
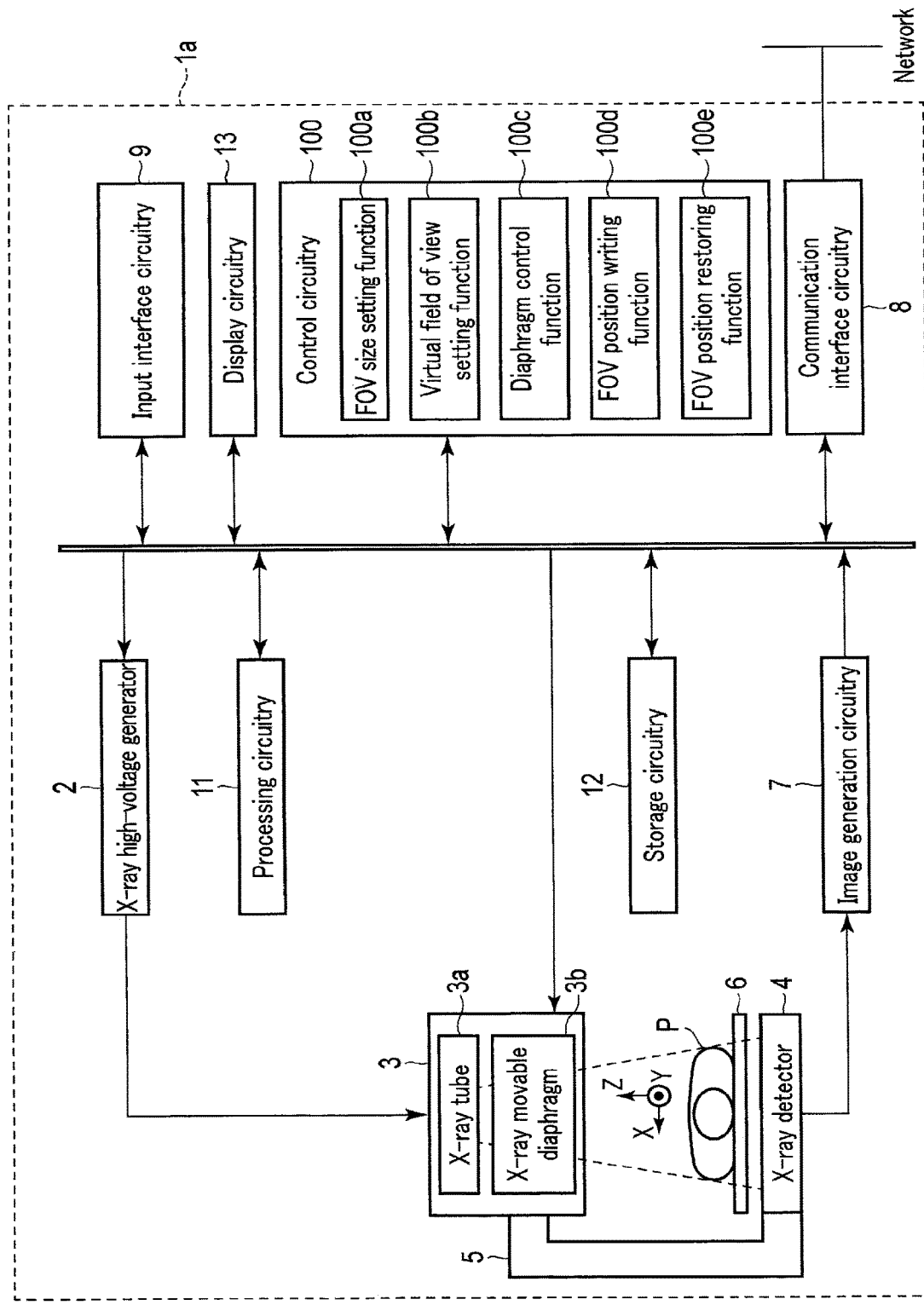
FIG. 12 is a block diagram showing one example of the configuration of an X-ray diagnostic apparatus according to a second embodiment.

FIG. 12 is a block diagram showing a configuration example of an X-ray diagnostic apparatus 1a according to a second embodiment. The X-ray diagnostic apparatus 1a includes an X-ray high-voltage generator 2, an X-ray source device 3, an X-ray detector 4, a support frame 5, a bed having a table top 6, an image generation circuitry 7, a communication interface circuitry 8, an input interface circuitry 9, a control circuitry 100, a processing circuitry 11, a storage circuitry 12, and a display circuitry 13. The X-ray source device 3 includes an X-ray tube 3a and an X-ray movable diaphragm 3b. The X-ray diagnostic apparatus 1a corresponds to an X-ray fluoroscopic diagnosis apparatus for use, for example, in digestive tract angiographic examinations, etc. The X-ray diagnostic apparatus 1a may be an X-ray fluoroscopic diagnosis apparatus for circulatory organs for use, for example, in angiographic examinations.

The X-ray high-voltage generator 2 generates a tube current to be supplied to the X-ray tube 3a and a tube voltage to be applied to the X-ray rube 3a. The X-ray high-voltage generator 2 supplies, to the X-ray tube 3a, tube currents suitable for the X-ray imaging and for the X-ray fluoroscopy, and applies, to the X-ray tube 3a, tube voltages suitable for the X-ray imaging and for the X-ray fluoroscopy, under the control of the control circuitry. The X-ray high-voltage generator 2 corresponds, for example, to a high-voltage generator based on an inverter control method.

The X-ray tube 3a generates X-ray based on the tube current applied from the X-ray high-voltage generator 2 and the tube voltage applied from the X-ray high-voltage generator 2. The X-ray generated by the X-ray tube 3a is applied to a subject P. The X-ray tube 3a corresponds, for example, to a rotating anode type X-ray tube. Also, the X-ray tube 3a may be, for example, a fixed anode X-ray tube, etc.

Hereinafter, a central axis along which X-ray is applied is denoted by a Z-axis. An axis that is perpendicular to the Z-axis and is in a longitudinal direction of the table top 6 is denoted by a Y-axis, and an axis perpendicular to the Z-axis and the Y-axis is denoted by an X-axis.

The X-ray movable diaphragm 3b limits the irradiation field of the X-ray generated by the X-ray tube 3a. The X-ray movable diaphragm 3b can apply X-ray only to an imaging region (or imaging range) of a subject P desired by the operator, by limiting the irradiation field of the X-ray. That is, the X-ray movable diaphragm 3b can prevent a region (or a range) different from the imaging region (or imaging range) from being subjected to unnecessary exposure. Also, the X-ray movable diaphragm 3*b* can reduce scattered X-ray and remove off-focus X-ray. Hereinafter, the wording, "limiting the irradiation field of X-ray" may be mutually referred to as "shielding X-ray" and "limiting down X-ray".

The X-ray movable diaphragm 3*b* has an unillustrated beam-limiting mechanism. The beam-limiting mechanism includes, for example, a pair of diaphragm blades that limit X-ray spreading in the X-axis direction, and a pair of beam-limiting blades that limit X-ray spreading in the Y-axis direction. The beam-limiting mechanism may control each of the diaphragm blades asymmetrically, or may control each of the pairs of diaphragm blade symmetrically. For example, the beam-limiting mechanism may be a mechanism in which all the diaphragm blades independently move from one another, or a mechanism in which two pairs of diaphragm blades move left-right symmetrically and up-down symmetrically. Also, the beam-limiting mechanism may have a multilayered structure by providing the four diaphragm blades in the Z-axis direction.

The X-ray detector 4 detects X-ray that has been generated from the X-ray tube 3*a* and has transmitted through a subject P. The X-ray detector 4 includes a flat panel detector (FPD) capable of detecting X-ray. The FPD includes a plurality of semiconductor detection elements. As semiconductor detection elements, there are an indirect conversion form and a direct conversion form. The indirect conversion form is a form of converting emitted X-ray into light by a scintillator such as a fluorescent substance and converting the converted light into an electric signal. The direct conversion form is a form of directly converting emitted X-ray into an electric signal. An image intensifier may be adopted for the X-ray detector 4. In this specification, the X-ray detectable range or a range inn which X-ray is detected, in the X-ray detector 4, is referred to as "X-ray detection region".

Electrical signals generated by a plurality of semiconductor detection elements along with the emission of X-ray are output to an unillustrated Analog-to-Digital converter (A/D converter). The A/D converter converts electric signals into digital data. The A/D converter outputs the digital data to the image generation circuitry 7.

In this specification, for example, fields of view of four types of FOV size are defined, in descending order of irradiation field, as Normal field of view N0, wide field of view M1, medium field of view M2, and narrow field of view M3. The normal field of view N0 relates, for example, to an irradiation field in which X-ray can be detected from the entire surface of an X-ray detection region. The wide field of view M1 relates to an irradiation field narrower than the irradiation field of the normal field of view N0. The medium field of view M2 relates to an irradiation field narrower than the irradiation field of the wide field of view M1. The narrow field of view M3 relates to an irradiation field narrower than the irradiation field of the medium field of view M2. Since the FOV sizes are associated with the size of the irradiation field, "the FOV size widens" relates to "the irradiation field widens".

An X-ray image corresponding to each of the FOV sizes is displayed to fit with a display window of the later-mentioned display (for example, in a magnified state). Specifically, a display based on the wide field of view M1 is displayed to be magnified as compared with the display based on the normal field of view N0. Therefore, switching the FOV size is synonymous with switching the magnification ratio of an image displayed on a display window. If the respective fields of view N0 to M3 are arranged in descending order of magnification ratio, it results in M3, M2, M1, and N0.

The support frame 5 movably supports the X-ray source device 3 and the X-ray detector 4 that are placed opposite to one another. Specifically, the support frame 5 corresponds to a frame of over-tube type where the X-ray source device 3 is upwardly disposed with respect to the surface of the table top 6. As the support frame 5, a frame of an under tube type where the X-ray source device 3 is downwardly disposed with respect to the surface of the table top 6 may be adopted. Also, as the support frame 5, a structure based on a C arm or an a-arm may be adopted. Furthermore, as the support frame 5, a structure using two arms (e.g., robot arms, etc.) independently supporting each of the X-ray source device 3 and the X-ray detector 4 may be adopted.

The bed not illustrated in the figure includes a table top 6 (also referred to as a spine table) on which a subject P is placed.

An unillustrated drive device drives the support frame 5 and the bed, respectively, for example, by the control of the control circuitry 100. During X-ray fluoroscopy and during X-ray photography, a subject P placed on the table top 6 is placed between the X-ray source device 3 and the X-ray detector 4. Also, the drive device drives the X-ray diaphragm 3*b*, for example, by the control of the control circuitry 100. The drive device may rotate the X-ray detector 4 with respect to the X-ray source device 3, under the control of the control circuitry 100.

The image generation circuitry 7 generates an X-ray image, based on digital data output from the X-ray detector 4 via the A/D converter. The image generation circuitry 7 outputs the generated X-ray image to the processing circuitry 11, the storage circuitry 12, an unillustrated external storage device, etc.

The communication interface circuitry 8 is a circuitry relating to, for example, a network, and the unillustrated external storage device. An X-ray image, etc. obtained by the X-ray diagnostic apparatus 1*a* can be transferred to other devices via the communication interface circuitry 8 and a network. Hereinafter, when information is exchanged via the communication interface circuitry 8, the description, "via the communication interface circuitry 8" is omitted.

The input interface circuitry 9 inputs X-ray irradiation conditions, such as imaging conditions for X-ray imaging and fluoroscopic conditions for X-ray fluoroscopy, desired by the operator; a fluoroscopy/imaging position; an irradiation field; and a region of interest (ROI) in an X-ray image, etc. in response to operator's instructions. Specifically, the input interface circuitry 9 relays various instructions, commands, information, selection, and settings from the operator into the X-ray diagnostic apparatus 1*a*.

The input interface circuitry 9 is implemented by a joystick for performing settings of a region of interest, etc., a track ball, a switch button, a mouse, a keyboard, a touch pad for performing input operations by touching an operation surface, a touch panel display in which a display screen is integrated with a touch pad, a foot switch for imaging, and a microphone for sound recognition, etc. The input interface circuitry 9 is connected to the control circuitry 100 and converts an input operation received from the operator into an electric signal to output it to the control circuitry 100.

In this specification, the input interface circuitry 9 is not limited to the one that includes physical operation components such as a mouse and a keyboard. For example, an electric signal processing circuitry that receives an electric signal corresponding to an input operation from an external input device provided separately from the X-ray diagnostic apparatus and outputs this electric signal to the control circuitry 100 is also encompassed in examples of the input interface circuitry 9.

The control circuitry 100 is a processor to control, for example, various circuitries and a drive device in the X-ray diagnostic apparatus 1a. The control circuitry 100 temporarily stores, in an unillustrated memory, information such as operator's instructions input from the input interface circuitry 9. The control circuitry 100 controls the X-ray high-voltage generator 2, the X-ray movable diaphragm 3b, and the drive device, etc. to implement X-ray imaging and X-ray fluoroscopy in accordance with operator's instructions stored in the memory. Also, the control circuitry 100 controls X-ray image generation processing in the image generation circuitry 7, and image generation processing in the processing circuitry 11, etc.

Furthermore, the control circuitry 100 executes various functions for performing settings and control relating to FOV sizes and FOV positions in accordance with operator's instructions stored in the memory. Examples of the various functions include a field of view size setting function (hereinafter, referred to as FOV size setting function) 100a, a field of view position setting function (hereinafter, referred to as FOV position setting function) 100b, a diaphragm control function 100c, a field of view position writing function (hereinafter, referred to as FOV position writing function) 100d, and a field of view position restoring function (hereinafter, referred to as FOV position restoring function) 100e, etc.

The FOV size setting function 100a sets one of a plurality of FOV sizes relating to the irradiation field of X-ray by operator's instructions. Specifically, the FOV size setting function 100a sets a first FOV size (e.g., corresponding to a wide field of view M1) of the plurality of FOV sizes relating to the irradiation field of X-ray. At that time, the operator selects a discretional FOV size (or a discretional magnification ratio) by pressing down a switch button of an input interface circuitry 9. As a method of selecting an FOV size, a method of selecting it by touching a touch panel, and a method of selecting it by sound recognition may be used.

The FOV position setting function 100b sets an FOV position by operator's instructions. Specifically, the FOV position setting function 100b sets, for example, a first field of view corresponding to a first FOV size set by the FOV size setting function 100a to a first FOV position within the X-ray detection region of the X-ray detector 4. At that time, the operator moves the field of view to a position, for example, by operating a joystick of the input interface circuitry 9. In other words, the FOV position setting function 100b has a function to read out an FOV position corresponding to the FOV size set by the FOV size setting function 100a from the storage circuitry 12 and to adjust the read out FOV position in accordance with operator's operations. The "field of view" in this specification is synonymous with an image to be displayed on the later explained display. The "FOV position" in this specification is a discretional position in which a field of view falls within an X-ray detection region.

Settings of FOV sizes and FOV positions may be performed by operator's operations, using a reference image generated in the later explained processing circuitry 11. The operator can simultaneously set an FOV size and an FOV position, for example, by selecting a desired range (or position) from a reference image displayed on the display and selecting a discretional FOV size centering on the desired range.

The diaphragm control function 100c controls the X-ray movable diaphragm 3b based on the field of view at the FOV position set by the FOV position setting function 100b. Specifically, for example, the diaphragm control function 100c controls the X-ray movable diaphragm 3b based on the first field of view at the first FOV position set by the FOV position setting function 100b. More specifically, the diaphragm control function 100c controls the X-ray movable diaphragm 3b based on the FOV size set by the FOV size setting function 100a, and a final FOV position read from or adjusted by the FOV position setting function 100b.

The FOV position writing function 100d writes, in the storage circuitry 12, etc., the adjusted final FOV position in such a manner that the adjusted final FOV position is associated with the set FOV size. Specifically, the FOV position writing function 100d writes the final FOV position, for example, taking switching, by means of the FOV size setting function 100a, to a second FOV size (e.g., corresponding to a medium field of view M2) different from the set first FOV size as a trigger. In this regard, however, the point of time of writing the FOV position is not limited to a point of time of setting switching between FOV sizes, and may be a point of time when the FOV position is adjusted. In this specification, the second FOV size is not limited to the FOV size of the medium field of view M2, and it may be set to an FOV size corresponding to any of a normal field of view N0, a wide field of view M1, and a narrow field of view M3. It is sufficient that the first FOV size is an FOV size different from the second FOV size.

The FOV position writing function 100d may be configured to further associate X-ray conditions relating to an FOV size with the FOV size and an FOV position, and to write the X-ray conditions, FOV size and the FOV position in the storage circuitry 12, etc. Specifically, FOV position writing function 100d may be configured to write X-ray conditions directly, or write, as the X-ray conditions, identification information in a condition table where X-ray conditions are set.

The FOV position restoring function 100e reads out an FOV position associated with the FOV size from the storage circuitry 12, etc., taking an FOV size that was selected in the past by the FOV size setting function 100a being reset as a trigger. With this, the FOV position restoring function 100e restores the past FOV position corresponding to the FOV size selected in the past.

The processing circuitry 11 includes, as hardware resource, a processor and a memory. The processing circuitry 11 reads out a control program stored in the storage circuitry 12 in accordance with starting instructions input by the operator via the input interface circuitry 9. The processing circuitry 11 implements image processing for displaying an X-ray image generated by the image generation circuitry 7 on the display, in accordance with the read out control program. Examples of the image processing include processing of cutting out an image only within a range where X-ray is applied and magnifying the cut-out image to a display region of a display.

Furthermore, the processing circuitry 11 may be configured to generate a reference image showing a position of an FOV size set for an X-ray detection region (normal field of view). Specifically, the processing circuitry 11 generates a reference image, for example, by using, an X-ray image preliminarily obtained in a normal field of view (or a still image acquired from a fluoroscopic image), and superimposing, on the image, an acquired frame line representing an FOV size. If there is no acquired X-ray image, a frame line indicating the outer frame of the X-ray detection region (normal field of view) may be displayed instead of the X-ray image, on a reference image.

The storage circuitry 12 is composed of memories for recording electric information, such as a hard disk drive (HDD), and peripheral circuitries such as a memory controller, and a memory interface accompanied by the memories. The memories are not limited to a HDD, and as the memories, a solid state drive (SSD), magnetic disk (e.g., Floppy Disk™ and hard disk), an optical disk (CD, DVD, Blu-Ray™, etc.), and a semiconductor memory can be suitably used.

Also, the storage circuitry 12 stores information in which various X-ray images generated by the image generation circuitry 7 are associated with the FOV sizes and FOV positions transmitted from the control circuitry 100, reference images processed in the processing circuitry 11, a system control program of the X-ray diagnostic apparatus 1a, a diagnostic protocol executed at the control circuitry 100, operator's instructions sent from the input interface circuitry 9, various data constellation, such as imaging conditions for X-ray imaging and fluoroscopy conditions for X-ray fluoroscopy, error information, and various data transmitted via a network, etc.

Herein, among the stored contents of the storage circuitry 12, information in which an FOV size is associated with an FOV position is explained using FIG. 13A to FIG. 13C. As shown in FIG. 13A, the storage circuitry 12 associates various FOV sizes relating to the irradiation field of X-ray with various FOV positions for positioning, in the x-ray detection region, fields of view corresponding to the FOV sizes, and stores the information.

In FIG. 13A, the values for FOV size "N0" indicate FOV sizes of normal fields of view NO. The values for FOV size "M1" indicate FOV sizes of wide fields of view of M1, M1a, and M1p. Since the wide fields of view M1, M1a, and M1p are fields of view with the magnification ratio being equal to each other, the values of FOV size "M1" are also equal to each other. The values for field of view "M2" indicate FOV sizes of medium fields of view M2, M2a, M2b, and M2c. Since the medium fields of view M2, M2a, M2b, and M2c are fields of view with the magnification ratio being equal to each other, the values of FOV size "M2" are also equal to each other. The values for field of view "M3" indicate FOV sizes of narrow fields of view M3. In FIG. 13A, the values of FOV positions are values of x-y coordinates indicating the center position of the field of view corresponding to the FOV position.

The storage circuitry 12 may store X-ray conditions relating to each of FOV sizes, XC0, . . . , XC3 in such a manner that these X-ray conditions are further associated with each of the FOV sizes and each of the FOV positions, as shown in FIG. 13B. In FIG. 13B, the values of X-ray conditions "XC0", . . . "XC3" are identification information of, for example, unillustrated four condition tables where X-ray conditions are set. The illustrated values, "XC0", "XC3" are not limited thereto, and may be values indicating X-ray conditions respectively indicating, a tube voltage, a tube current, etc. Also the storage circuitry 12 may associate a predetermined FOV size and a plurality of FOV positions and store them, as shown in FIG. 13C. Alternatively, the storage circuitry 12 may associate a predetermined FOV size, a plurality of FOV positions and X-ray conditions, and store them (not illustrated).

The display circuitry 13 is composed of a display for displaying medical images, an internal circuitry for supplying a display signal to the display, and peripheral circuitries, such as a connector or a cable that connects the display and the internal circuitry.

The display displays X-ray images (radiographic images or fluoroscopic images) generated by the image generation circuitry 7, or display images processed by the processing circuitry 11. As for the display, the entire surface of the display may be used as a display window for displaying X-ray images, or part of the display may be used as a display window, or the display may be configured to switch between the entire surface thereof and part of the entire surface thereof. Also, the display may display an X-ray image and a reference image in parallel on a display window. The display may further display input screens relating to inputs of fluoroscopy/imaging positions, X-ray irradiation conditions, etc. Also, the display may display, for example, an X-ray image and input screens in parallel on a display window, and may display, an X-ray image, a reference image, and input images in parallel on a display window.

Figure 14:
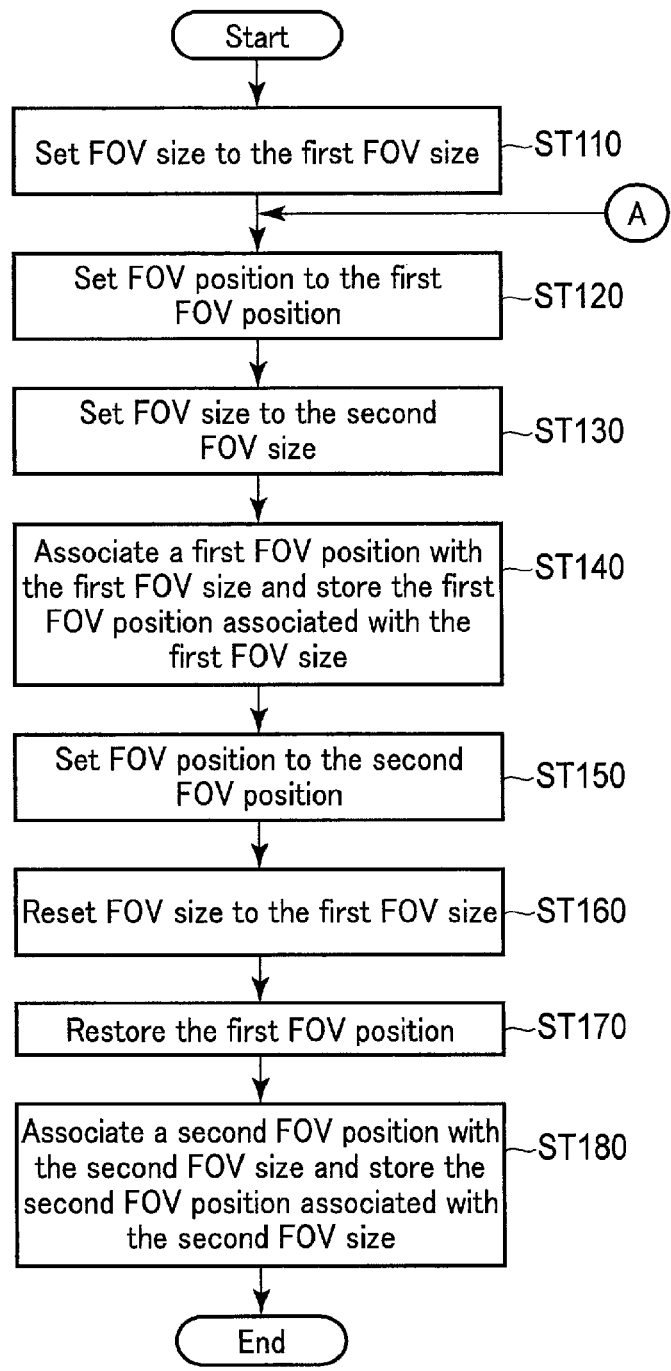
FIG. 14 is a flowchart for illustrating the operations of a control circuitry in the second embodiment.

Next, the operations of the X-ray diagnostic apparatus 1a configured as above will be described using the flowchart of FIG. 14, and the display images, etc. shown in FIG. 15. The following are mainly explanations on settings and control relating to FOV sizes and FOV positions by the control circuitry 100.

First, a subject P is placed on the table top 6 of the bed. In the X-ray diagnostic apparatus 1a, a preset examination type and a preset examination name are selected, and fluoroscopy conditions (X-ray conditions) associated with the selected examination type and examination name are set, by operator's operations. Thereafter, the X-ray diagnostic apparatus 1a starts X-ray fluoroscopy with the normal field of view N0 by operator's operations. Namely, an X-ray tube 3a generates X-ray, a diaphragm control function 100c controls an X-ray movable diaphragm 3b based on the FOV size and FOV position of the normal field of view N0 to limit the irradiation field of the X-ray. The X-ray whose irradiation field is limited is transmitted through the subject P and is detected by an X-ray detector 4. An image generation circuitry 7 generates an X-ray image based on an output of the X-ray detector 4. A display circuitry 13 displays an X-ray image of the normal field of view NO. Thereafter, step ST110 is started.

In the step ST110, an FOV size setting function 100a sets the FOV size to a first FOV size by operator's operations. At this time, the operator selects a discretional FOV size (or a discretional magnification ratio), for example, by pressing down a switch button of the input interface circuitry 9. The selection of an FOV size may be referred to as switching of FOV sizes.

Specifically, as illustrated in FIG. 15 (a), the FOV size setting function 100a sets an FOV size of a wide field of view M1 that is different from the FOV size of the normal field of view employed at the start point. The diaphragm control function 100c controls an X-ray movable diaphragm 3b based on the FOV size and FOV position. At this time, a display image 210 of a wide field of view M1 becomes an image magnified toward the center of the image based on the normal field of view NO. This is because an FOV position corresponding to the first FOV size is not stored in the storage circuitry 12 when the first FOV size is set for the first time after the start of X-ray fluoroscopy.

In step ST120, the FOV position setting function 100b suitably sets the adjusted FOV position to a first FOV position by operator's operations. At that time, the operator moves the wide field of view M1 to a desired position (Region of Interest (ROI)), for example, by operating a joystick of the input interface circuitry 9.

Specifically, as illustrated in FIG. 15 (*b*), the FOV position setting function 100*b* suitably adjusts the FOV position of the wide field of view M1 to set an FOV position of a wide field of view M1*a*. The diaphragm control function 100*c* controls the X-ray movable diaphragm 3*b* based on the FOV size and the adjusted FOV position. At that time, a display image 220 of the wide field of view M1*a* becomes an image whose FOV position is moved while maintaining the magnification ratio of the display image 210 of the wide field of view M1.

In step ST130, the FOV size setting function 100*a* sets the FOV size to a second FOV size by operator's operations.

Specifically, as illustrated in FIG. 15 (*c*), the FOV size setting function 100*a* sets an FOV size of a medium field of view M2 that is different from the FOV size of the wide field of view M1*a*. A diaphragm control function 100*c* controls the X-ray movable diaphragm 3*b* based on the FOV size and FOV position. At that time, a display image 230 of the medium field of view M2 becomes an image magnified toward the center of the display image 220 of the wide field of view M1*a*. This is because, similarly to the above, an FOV position corresponding to the second FOV size is not stored in the storage circuitry 12 when the second FOV size is set for the first time.

In step ST140, a FOV position writing function 100*d* associates the first FOV position before the setting of switching from the first FOV size to the second FOV size with the first field of view, and stores the information in the storage circuitry 12, etc., taking the setting of switching from the first FOV size to the second FOV size as a trigger.

In step ST150, the FOV position setting function 100*b* suitably sets the adjusted FOV position to the second FOV position by operator's operations.

Specifically, as illustrated in FIG. 15(*d*), the FOV position setting function 100*b* suitably adjusts the FOV position of the medium field of view M2 to set an FOV position of a the medium field of view M2*a*. The diaphragm control function 100*c* controls the X-ray movable diaphragm 3*b* based on the FOV size and the adjusted FOV position. At that time, a display image 240 of the medium field of view M2*a* becomes an image whose FOV position is moved while maintaining the magnification ratio of the display image 230 of the medium field of view M2.

In step ST160, the FOV size setting function 100*a* resets the FOV size to the first FOV size by operator's operations.

In step ST170, an FOV position restoring function 100*e* reads out the first FOV position associated with the first FOV size from the storage circuitry 12, taking the resetting of the first FOV size by the FOV size setting function 100*a* as a trigger. With this, the FOV position restoring function 100*e* restores the first FOV position.

Specifically, as illustrated in FIG. 15(*e*), the FOV position restoring function 100*e* reads an FOV position corresponding to the FOV size of the wide field of view M1*a*, taking the resetting of the FOV size of the wide field of view M1*a* as a trigger. With this, the FOV position of the wide field of view Mia is set (restored). The diaphragm control function 100*c* controls the X-ray movable control function 3*b*, based on the FOV size, and the restored FOV position. At that time, a display image 250 of the wide field of view M1*a* having the restored FOV position becomes substantially the same image as the display image 220 of the wide field of view M1*a* having the FOV position stored in step ST140. Note that substantially the same image indicates an image fluoroscoped (or imaged) in a state where the FOV size and the FOV position substantially agree with those of another image; however, a change in display image itself attributable to the movement of a subject P, etc. is not taken into consideration.

In step ST180, the FOV position writing function 100*d* associates a second FOV position before resetting with the second FOV size and stores the second FOV position in the storage circuitry 12, etc., taking the resetting of switching from the second field of view to the first FOV size as a trigger.

As described above, according to the second embodiment, the X-ray diagnostic apparatus includes a memory that stores an FOV size in association with an FOV position, the FOV size being related to the irradiation field, the FOV position being within the X-ray detection region. Also, the X-ray diagnostic apparatus sets the FOV size. Furthermore, the X-ray diagnostic apparatus reads out, from the memory, the FOV position associated with the set FOV size to control the x-ray movable diaphragm, based on the FOV size and the FOV position.

Therefore, by the configuration of the X-ray diagnostic apparatus capable of controlling an X-ray movable diaphragm based on the set FOV size and the read out FOV position associated with this FOV size, the FOV position that was set before can be maintained when an FOV size is switched.

In addition to the above, according to the second embodiment, the X-ray diagnostic apparatus adjusts the FOV position corresponding to a set FOV size in response to operator's operations and writes the finally adjusted FOV position in association with the set FOV size in the memory. The X-ray diagnostic apparatus writes the finally adjusted FOV position, taking setting of switching to an FOV size different from the set FOV size as a trigger. Therefore, since the X-ray diagnostic apparatus can store an FOV size before switching and an FOV position before switching in such a manner that the FOV size and the FOV position are associated with one another, taking setting of switching of an FOV size as a trigger, it can maintain an FOV position that was set before also at the time of switching an FOV size. With this configuration, the setting of an FOV position that can occur every time an FOV size is switched can be omitted, and an improvement in working efficiency and a reduction in unnecessary exposure can be expected. This advantage can be expected also in a case where an FOV position is written when the FOV position is adjusted.

According to the second embodiment, the X-ray diagnostic apparatus can reuse an FOV position that was set before by restoring a first FOV position associated with a first FOV size, taking resetting of the first FOV size as a trigger.

Furthermore, according to the second embodiment, the X-ray diagnostic apparatus may be configured to store the X-ray conditions related to each of the FOV sizes in association with each of the FOV sizes and each of the FOV positions, as shown in FIG. 13B. Specifically, when the FOV position corresponding to an FOV size before switching is written in the storage circuitry 12, the X-ray conditions before the switching are also written in the storage circuitry 12 in such a manner that the X-ray conditions are associated with the FOV size before the switching. In this case, since an FOV position and X-ray conditions in accordance with the FOV size can be restored, appropriate X-ray conditions can be set (restored) for each FOV size, and stable X-ray images (radiographic images or fluoroscopic images) can be obtained. The X-ray diagnostic apparatus may be configured to display, on the screen, a message for urging the operator to authorize the setting of the X-ray conditions before the X-ray conditions associated with the FOV size are set (used).

Third Embodiment

Next, an X-ray diagnostic apparatus according to a third embodiment will be described.

The third embodiment is a modification example of the second embodiment, and is configured to preliminarily set an initial position for a specific FOV position among various FOV positions stored in a storage circuitry 12. The initial position may be referred to as a preset position.

Herein, an FOV size setting function 100*a* sets any of a plurality of FOV sizes relating to the irradiation field of X-ray by operator's operations. Furthermore, the FOV size setting function 100*a* outputs information of the set FOV size to an FOV position restoring function 100*e*.

The FOV position restoring function 100*e* determines whether or not the initial position of the specific FOV position preliminarily associated with the FOV size is present received from the FOV size setting function 100*a*. If the initial position is present therein, the FOV position restoring function 100*e* restores the initial position of the specific FOV position associated with the received FOV size, and if the initial position is not present therein, the FOV position restoring function 100*e* stands by until it receives any operator's operation. In other words, if an initial position of a specific FOV position is preliminarily associated with a received FOV size (e.g., a first FOV size), the FOV position restoring function 100*e* restores a specific FOV position associated with the first FOV size, which was associated by the FOV size setting function 100*a*.

Herein, a presetting method for preliminarily setting an initial position to a specific FOV position associated with a certain FOV size is described. Note that as a presetting method, it is sufficient that a processing circuitry 11 (or a control circuitry 100) includes a presetting function to execute a presetting method. For example, the presetting method can be realized by storing a program for executing the presetting function in the storage circuitry 12, and reading out the program by the processing circuitry 11 (or a control circuitry 100).

Figure 16A:
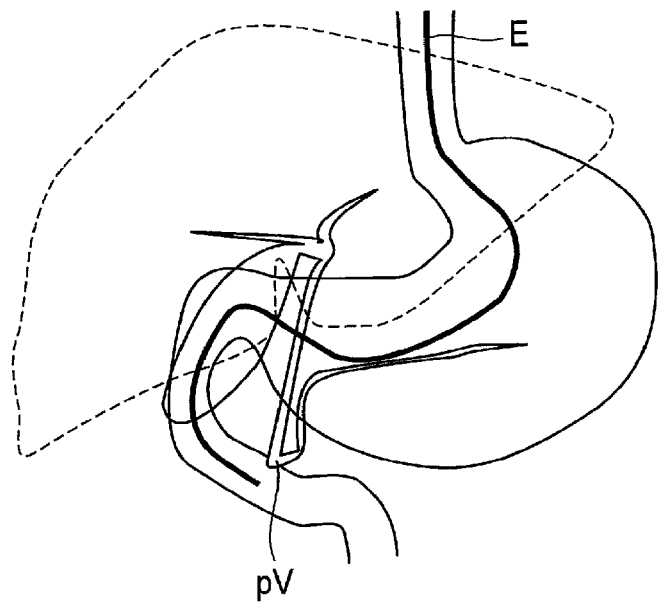
FIG. 16A is a diagram exemplarily showing the relationship between an assumed position of an internal organ and the position of an endoscope, according to a third embodiment.

Herein, a first presetting method is a method of setting, in the storage circuitry 12, an initial position of a specific FOV position, based, for example, on an anatomical position relationship according to each of various sorts of examination by operator's operations. As such an examination, an examination based on Endoscopic Retrograde Cholangio Pancreatography (ERCP) as illustrated in FIG. 16A is assumed.

Figure 16B:
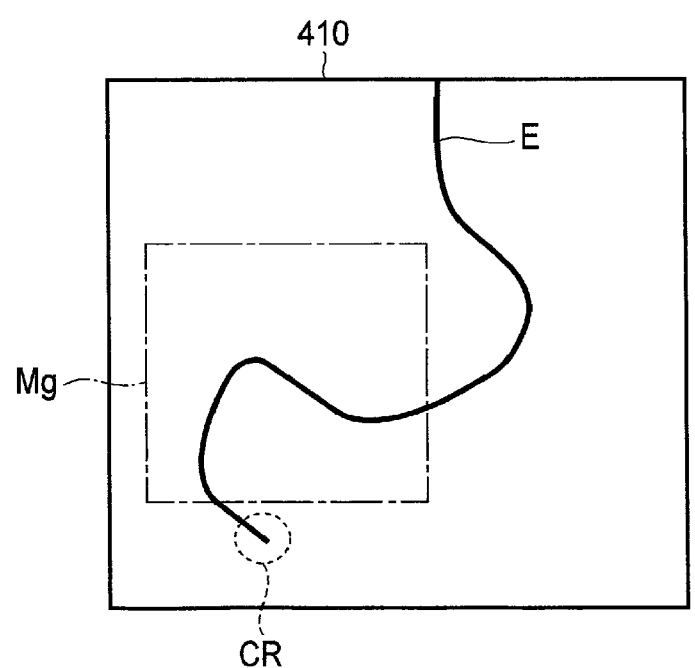
FIG. 16B is a diagram exemplarily showing the relationship between a reference point and an FOV position corresponding to FIG. 16A.

In an ERCP examination, an operator inserts an endoscope E from the mouth of a subject P to the intestine duodenum and confines a distal end of the endoscope E near the papilla Vater pV. Next, the operator starts X-ray fluoroscopy with a normal field of view, moves an X-ray source device 3 so that a predetermined source image distance (SID) is set, and moves the X-ray source device 3 to a place where the distal end of the endoscope E is positioned at a reference marker CR of a reference image 410 illustrated in FIG. 16B. The operations described above are positioning for setting.

After completion of the positioning, the processing circuitry 11 calculates a specific FOV position, for example, from an anatomical position relationship with respect to the papilla Vater pV. Specifically, the processing circuitry 11 calculates a set field of view Mg that can capture the gallbladder as a region of interest (ROI), using, for example, the position of the reference marker CR and the SID in the normal field of view.

A second presetting method is a method of setting an initial position of a specific FOV position in the storage circuitry 12, based, for example, on the positional relationship between the initial position and a region corresponding to the entire surface of an X-ray detection region of the X-ray detector 4, by operator's operations. Specifically, the operator can set an initial position of a specific FOV position corresponding to a predetermined FOV size by selecting a range corresponding to the predetermined FOV size from a reference image corresponding to the normal field of view.

Figure 17:
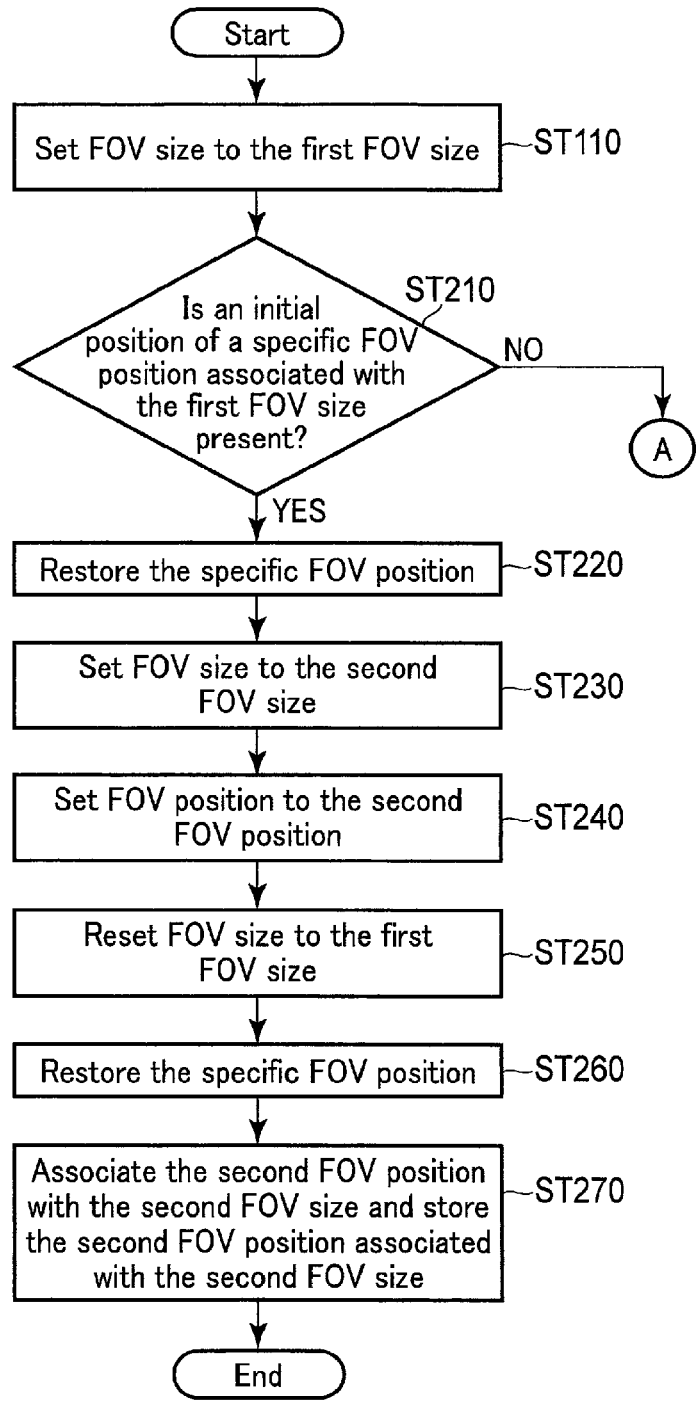
FIG. 17 is a flowchart for illustrating the operations of a control circuitry in the third embodiment.

Next, the operations of the X-ray diagnostic apparatus 1*a* configured as above are described using the flowchart of FIG. 17 and the display images shown in FIG. 18, etc. The following explanations are mainly for settings relating to FOV sizes and FOV positions by the control circuitry 100.

First, a subject P is placed on a table top 6 of the bed. In the X-ray diagnostic apparatus 1*a*, a preset examination type and a preset examination name are selected, and fluoroscopy conditions associated with the selected examination type and examination name are set by operator's operations. Thereafter, the X-ray diagnostic apparatus 1*a* starts X-ray fluoroscopy with a normal field of view N0, as described above, by operator's operations and starts step ST110.

In step ST110, the FOV size setting function 100*a* sets the FOV size to a first FOV size, in replacement of the FOV size of the normal field of view N0 at the starting. Note that the first FOV size is assumed, for example, as an FOV size of a wide field of view M1*p*. Furthermore, the FOV size setting function 100*a* outputs information of the set first FOV size to an FOV position restoring function 100*e*. At that time, the operator selects a discretional FOV size (or a discretional magnification ratio) by pressing down a switching button of an input interface circuitry 9. The selection of an FOV size may be referred to as switching of an FOV size.

In step ST210, the FOV position restoring function 100*e* determines whether or not an initial position of a specific position preliminarily associated with the first FOV size received from the FOV size setting function 100*a* is present in the storage circuitry 12. If the initial position of the specific FOV position is present therein, the process proceeds to step ST220, and if the initial position of the specific FOV position is not present therein, the process proceeds to step ST120 shown in FIG. 14.

In step ST220, a FOV position restoring function 100*e* reads out, from the storage circuitry 12, the initial position of the specific FOV position associated with the first FOV size set in step ST110. With this, the FOV position restoring function 100*e* restores (the initial position of) the specific FOV position.

Specifically, as illustrated in FIG. 18(*a*), the FOV position restoring function 100*e* restores the specific FOV position associated with the set FOV size, based on the FOV size of the wide field of view M1*p* set in step ST110. A diaphragm control function 100*c* controls an X-ray movable diaphragm 3*b* based on the restored FOV position. At this time, a display image 310 of a wide field of view M1*p* becomes an image magnified to be larger than the normal field of view, and with the field of view being already moved to the specific FOV position. Thereafter, the specific FOV position is suitably adjusted by operator's operations to become a final FOV position.

In step ST230, the FOV size setting function 100a sets the FOV size to a second FOV size, in replacement of the first FOV size of the wide field of view M1p, by operator's operations.

Specifically, as illustrated in FIG. 18 (b), the FOV size setting function 100a sets an FOV size of a medium field of view M2 different from the FOV size of the wide field of view M1p. A diaphragm control function 100c controls the X-ray movable diaphragm 3b based on the FOV size and FOV position. At this time, a display image 320 of the medium field of view M2 becomes an image magnified toward the center of a display image 310 of the wide field of view M1p.

In step ST240, an FOV position setting function 100b suitably sets the adjusted FOV position to a second FOV position, by operator's operations.

Specifically, as illustrated in FIG. 18(c), the FOV position setting function 100b suitably adjusts the FOV position of the medium field of view M2 to set an FOV position of the medium field of view M2a. The diaphragm control function 100c controls the x-ray movable diaphragm 3b based on the FOV size and the adjusted FOV position. At this time, a display image 330 of the medium field of view M2a becomes an image whose FOV position is moved while maintaining the magnification ratio of the display image 320 of the medium field of view M2.

In step ST250, the FOV size setting function 100a resets the FOV size to the first FOV size by operator's operations.

In step ST260, the FOV position restoring function 100e reads out, from the storage circuitry 12, a specific FOV position associated with the first FOV size, taking the resetting of the first FOV size by the FOV size setting function 100a as a trigger. With this, the FOV position restoring function 100e restores a specific FOV position.

Specifically, as illustrated in FIG. 18(d), the FOV position restoring function 100e reads out a specific FOV position corresponding to the FOV size of the wide field of view M1p, taking the resetting of the FOV size of the wide field of view M1p as a trigger. With this, the specific FOV position of the wide field of view M1p is set (restored). The diaphragm control function 100c controls the X-ray movable diaphragm 3b based on the FOV size and the set FOV position. At this time, a display image 340 of the wide field of view M1p becomes substantially the same image as the display image 310 of the wide field of view M1p. Note that substantially the same image means an image that is fluoroscoped (or imaged) in a state where the FOV size and the FOV position are substantially the same as those of another image; however, a change in display image itself attributable to a movement of a subject P is not taken into consideration. In this respect, however, when an initial position is adjusted, a specific. FOV position read out taking resetting as a trigger, becomes an adjusted final FOV position, not the initial position.

In step ST270, the FOV position writing function 100d associates a second FOV position before resetting with the second FOV size, taking switching from the second FOV size to the first field of view by the FOV size setting function 100a as a trigger, and stores, in the storage circuitry 12, etc., the second FOV position before the resetting.

As explained above, according to the third embodiment, the X-ray diagnostic apparatus presets an initial position for a specific FOV position among various FOV positions stored in a memory. With this configuration, when an initial position of a specific FOV position is preliminarily associated with a first FOV size, the X-ray diagnostic apparatus restores the initial position of the specific FOV position associated with the first FOV size, taking the setting of the first FOV size as a trigger. Therefore, since the first FOV size is set for the first time, it is possible to omit the setting of a specific FOV position, and therefore, improvements in working efficiency and a reduction in unnecessary exposure are expected. In addition, in the second embodiment, if an FOV size is selected for the first time after the start of an examination, there is no FOV position corresponding to the FOV size, and therefore, an image is magnified or reduced with a central focus on the center of the screen. In contrast, according to the third embodiment, an FOV position (initial position) corresponding to an FOV size is preset, and therefore, an image can be magnified with a central focus on a region of interest, even when the FOV size is selected for the first time.

According to the third embodiment, the X-ray diagnostic apparatus sets an initial position of a specific FOV position, based on an anatomical position relationship according to each of various examinations. Therefore, the X-ray diagnostic apparatus according to the third embodiment can reduce the operator's burdens.

Furthermore, according to the third embodiment, the X-ray diagnostic apparatus sets an initial position of a specific FOV position, based on a positional relationship between the initial position and a region corresponding to the entire surface of an X-ray detection region. Therefore, the X-ray diagnostic apparatus can present a field of view without the need for an X-ray image (a radiographic image or fluoroscopic image).

Fourth Embodiment

Next, an X-ray diagnostic apparatus according to a fourth embodiment will be explained.

The fourth embodiment is a modification example of the second embodiment or the third embodiment, and as shown in FIG. 13C, it is configured to associate a plurality of FOV positions with a certain FOV size, and to store the plurality of FOV positions. The number of FOV positions associated with each FOV size may be the same or may be different, per FOV size, although this is not illustrated in the figure. For example, one FOV position is associated with each of certain two FOV sizes, and three FOV positions may be associated with each of the other two FOV sizes.

An FOV position writing function 100d may be configured to associate a predetermined FOV size with a plurality of predetermined FOV positions and to store, in a storage circuitry 12, etc., the predetermined FOV size and the plurality of predetermined FOV positions. At that time, the operator associates and stores the FOV size and FOV positions that are currently under development, for example, by pressing a discretional switch button of an input interface circuitry 9.

The method of allowing the FOV position writing function to store the information is not limited to during the time of fluoroscopy, the predetermined FOV size and a plurality of predetermined FOV positions are associated and stored by selecting a range corresponding to the predetermined FOV size plural times. Specifically, as illustrated in FIG. 19, a FOV position writing function 100d associates a predetermined FOV size with a plurality of predetermined FOV positions (medium field of views, M2a, M2b, and M2c) and stores them in the storage circuitry 12 by selecting, from a reference image 510, a range corresponding to a medium field of view M2 in rotation by operator's operations and stores them in the storage circuitry 12.

An FOV position restoring function 100e has a function to cyclically read out, from the storage circuitry 12, one of the plurality of FOV positions corresponding to the predetermined FOV size, every time a predetermined FOV size is set in succession, in addition to the functions described above. Specifically, the FOV position restoring function 100e cyclically restores the medium fields of view, M2a, M2b, and M2c, taking the same FOV size being set during display of an image with a second FOV size (corresponding to a medium field of view M2) as a trigger. As a method of setting the same FOV size, the operator may press a switch button corresponding to a change of the FOV size in the input interface circuitry 9, may select a plurality of predetermined FOV positions displayed on a reference screen by means of a touch panel of the input interface circuitry 9, and may instruct a plurality of predetermined FOV positions displayed on a reference screen by a spoken command through a sound recognition microphone of the input interface circuitry 9.

A processing circuitry 11 may generate a reference image corresponding to the entire surface of an X-ray detection region and indicating positions of one or more fields of view corresponding to a set FOV size. Specifically, the processing circuitry 11 generates a reference image, for example, by using a preliminarily acquired X-ray image with an FOV size corresponding to the entire surface (normal field of view) of an X-ray detection region, and superimposing one or more frame lines representing a field of view corresponding to the set FOV size on the X-ray image. More specifically, the processing circuitry 11 may display, in the reference image 510, frame lines indicating the medium fields of view, M2a, M2b, and M2c, as illustrated in FIG. 19.

Also, the processing circuitry 11 may perform processing for changing the line type of a frame line superimposed on a reference image. Specifically, as illustrated in FIG. 20, the processing circuitry 11 represents frame lines (medium fields of view, M2a, M2b, and M2c) superimposed and displayed on a reference image 610 with a solid line for a selected field of view (medium field of view M2a), and with a broken line for unselected fields of view (medium fields of view M2b, and M2c). In other words, the processing circuitry 11 performs processing for making the line type of a frame line representing a field of view corresponding to an FOV size that is currently under development different from the line type of the frame lines other than the frame line. With this, the currently selected field of view of a plurality of FOV positions can be clearly specified.

As for a display of a display circuitry 13, a reference image and a fluoroscopic image (live image) may be displayed in parallel on the display window. Specifically, the display displays, as illustrated in FIG. 20, the reference image 610 and a live image 620 in parallel on a display window 600. In the live image 620, the medium field of view M2a that is selected in the reference image 610 is displayed in a magnified state. In this respect, however, the above-mentioned reference images 510 and 610 are a discretionally added matter, and may be omitted. For example, if the reference image 610 is omitted, every time a predetermined FOV size is set in succession, the live image 620 corresponding to the predetermined FOV size is cyclically displayed on the display window 600 with no display of the reference image 610.

Figure 21:
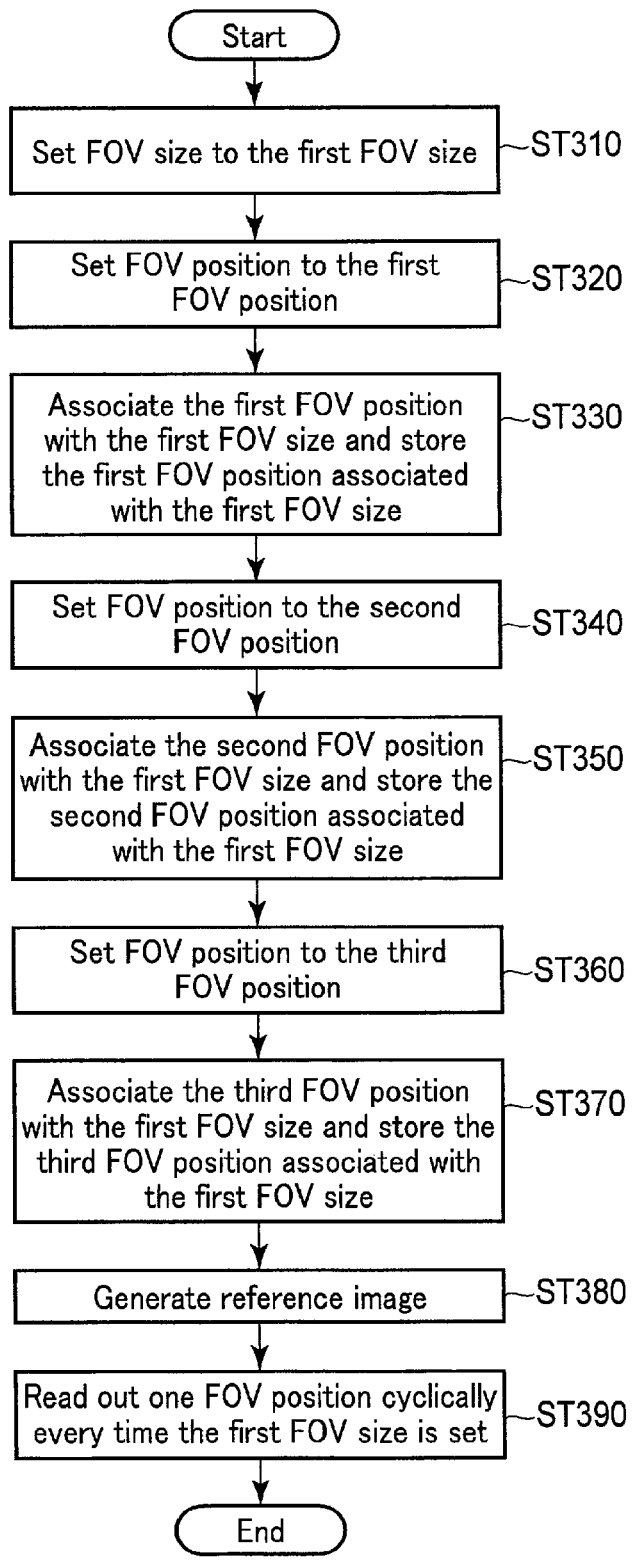
FIG. 21 is a flowchart for illustrating the operations of a control circuitry in the fourth embodiment.

Next, the operations of the X-ray diagnostic apparatus 1a configured as above are explained using the flowchart of FIG. 21 and the reference images shown in FIGS. 19 and 20, etc. The following explanations are mainly for settings and control related to FOV sizes and FOV positions by the control circuitry 100.

First, a subject P is placed on a table top 6 of the bed. In the X-ray diagnostic apparatus 1a, a preset examination type and a preset examination name are selected, and fluoroscopy conditions (X-ray conditions) associated with the selected examination type and examination name are set by operator's operation. Thereafter, the X-ray diagnostic apparatus 1a starts X-ray fluoroscopy with a normal field of view N0 in the same manner as described above by operator's operations, and suitably and preliminarily acquires a fluoroscopic still image as an X-ray image to be used for the reference images, 510 and 610. This X-ray image is suitably stored in the storage circuitry 12. Thereafter, the X-ray diagnostic apparatus 1a starts step ST310.

In step ST310, the FOV size setting function 100a sets the FOV size to a first FOV size by operator's operations. Furthermore, the FOV size setting function 100a outputs information of the set first FOV size to the FOV position setting function 100b. At that time, the operator selects a discretional FOV size (or a discretional magnification ratio), for example, by pressing a switch button of the input interface circuitry 9. The selection of afield of view may be referred to as switching of an FOV size.

In step ST320, the FOV position setting function 100b reads out, from the storage circuitry 12, an FOV position corresponding to the first FOV size and suitably sets the adjusted FOV position to a first FOV position by operator's operation. As an initial value of the FOV position corresponding to the first FOV size, for example, the center position of the normal field of view N0 may be set. When adjusting the FOV position, the operator moves the field of view to a desired position (a region of interest), for example, by operating a joystick of the input interface circuitry 9. Specifically, as illustrated in FIG. 19, the FOV position setting function 100b adjusts and sets the FOV position of a medium field of view M2a in accordance with operator's operations. Note that the read-out FOV position may be set without being adjusted.

In step ST330, the FOV position writing function 100d associates the first FOV size with the first FOV position and stores them in the storage circuitry 12, etc. by operators operations. At that time, the operator associates and stores the FOV size (the first FOV size) and first FOV position that are currently under development, for example, by pressing a switch button of the input interface circuitry 9.

In step ST340, the FOV position setting function 100b sets the FOV position to a second FOV position by operator's operations. Specifically, as illustrated in FIG. 19, the FOV position setting function 10b adjusts the FOV position of a medium field of view M2a and sets an acquired FOV position of the medium field of view M2b in accordance with operator's operations.

In step ST350, the FOV position writing function 100d associates the first FOV size with the second FOV position, and stores them in the storage circuitry 12, etc., by operator's operations. With this, the storage circuitry 12 stores two FOV positions (first and second FOV positions) associated with the first FOV size.

In step ST360, the FOV position setting function 100b sets the FOV position to a third FOV position by operator's operations. Specifically, as illustrated in FIG. 19, the FOV position setting function 100b adjusts the FOV position of the medium field of view M2b and sets an acquired FOV position of the medium field of view M2c.

In step ST370, the FOV position writing function 100d associates the first FOV size with a third FOV position, and stores them in the storage circuitry 12, etc., by operator's operations. With this, the storage circuitry 12 stores three FOV positions (the first to third FOV positions), while associating them with the first FOV size.

In step ST380, the processing circuitry 11 generates the reference image 610 indicating positions of three medium fields of view, M2a, M2b, and M2c corresponding to the set first FOV size. Specifically, as shown in FIG. 20, the processing circuitry 11 generates the reference image 610 by using a preliminarily acquired X-ray image with an FOV size of the normal field of view N0 and superimposing three frame lines representing the medium fields of view, M2a, M2b, and M2c corresponding to the first FOV size on the X-ray image. At that time, the processing circuitry 11 performs processing for making the line type of a frame line representing the medium field of view M2a corresponding to the first FOV size that is currently under development different from the line type of the frame lines other than this frame line. The diaphragm control function 100c controls the X-ray movable diaphragm 3b based on the FOV size and the FOV position. With this, the live image 620 corresponding to the FOV position is displayed in parallel with the reference image 610.

In step ST390, it is assumed that the first FOV size is set in succession by operator's operations. At that time, the FOV position restoring function 100e reads out, from the storage circuitry 12, one of the three FOV positions corresponding to the first FOV size in rotation, every time the first FOV size is set in succession. That is, the FOV position of the medium field of view M2a, the FOV position of the medium field of view M2b, and the FOV position of the medium field of view M2c are read out in rotation (M2a→M2b→M2c→M2a→m2b→M2c→M2a→ . . . ).

With this configuration, when the first FOV size is set, for example, the FOV position of the medium field of view M2a is restored. Subsequently, when the first FOV size is set, the FOV position of the medium field of view M2b is restored. Subsequently, when the first FOV size is set, the FOV position of the medium field of view M2c is restored. Furthermore, when the first FOV size is set, the FOV position of the medium field of view M2a is restored. In the following operations, every time the first FOV size is set, one of the three FOV positions corresponding to the FOV size is restored in rotation. Along with this operation, the diaphragm control function 100c controls the X-ray movable diaphragm 3b based on the FOV size and the restored FOV position. Therefore, the live image 620 corresponding to an FOV position is cyclically displayed.

As explained above, according to the fourth embodiment, the X-ray diagnostic apparatus associates a predetermined FOV size with a plurality of FOV positions and stores the FOV size and the FOV positions. The X-ray diagnostic apparatus cyclically reads out, from a memory, one of a plurality of FOV positions corresponding to a predetermined FOV size every time a predetermined FOV size is set in succession. Therefore, even when there are a plurality of regions of interest, it is possible to change a field of view simply.

According to the fourth embodiment, the X-ray diagnostic apparatus generates a reference image corresponding to the entire surface of the X-ray detection region and indicating positions of one or more fields of view corresponding to a set FOV size. Therefore, a plurality of FOV positions with respect to a normal field of view can be checked easily.

According to the fourth embodiment, the X-ray diagnostic apparatus generates a reference image by using an X-ray image preliminarily acquired with an FOV size corresponding to the entire surface of an X-ray detection region and superimposing, on the X-ray image, one or more frame lines representing a field of view corresponding to the set FOV size. Therefore, a plurality of FOV positions with respect to a normal field of view can be visually checked with ease.

Furthermore, according to the fourth embodiment, the X-ray diagnostic apparatus performs processing for making a line type of a frame line representing a field of view corresponding to an FOV size that is currently under development different from a line type of frame lines other than this frame line. With this configuration, it is possible to easily determine in what position an X-ray image (a radiographic image or fluoroscopic image) that is currently displayed is positioned in the normal field of view.

The "processor" mentioned above includes, for example, a central processing unit (CPU), graphics processing unit (GPU), and a circuitry such as an application specific integrated circuitry (ASIC) or programmable logic device (e.g., simple programmable logic device (SPLD), complex programmable logic device (CPLD), and field programmable gate array (FPGA)).

The processor realizes the functions by reading and implementing the programs stored in the storage circuitry 31, which are explained later. Instead of storing the programs in the storage circuitry 31, the programs may be directly loaded in the circuitry of the processor. In such a configuration, the processor reads and implements the programs loaded in the circuitry to realize the various functions.

Each of the processors according to the present embodiment does not always have to be configured as a single circuitry, but a single processor may be provided by combining a plurality of independent circuitries to realize their functions. In addition, a plurality of structural components may be incorporated into one processor to realize their functions. For example, the processor of the control circuitry 1000 and the processor of the processing circuitry 11 may be integrated into one processor. Furthermore, the processor of the image generation circuitry 7, the processor of the control circuitry 1000, and the processor of the processing circuitry 11 may be integrated into one processor.

Fifth Embodiment

FIG. 22 is a block diagram showing a configuration example of an X-ray diagnostic apparatus 1b according to a fifth embodiment. The X-ray diagnostic apparatus 1b includes an X-ray high-voltage generator 2, an X-ray source device 3, an X-ray detector 4, a support frame 5, a bed having a table top 6, an image generation circuitry 7, a communication interface circuitry 8, an input interface circuitry 9, a control circuitry 1000, a processing circuitry 11, a storage circuitry 12, and a display circuitry 13. The X-ray source device 3 includes an X-ray tube 3a and an X-ray movable diaphragm 3b. The X-ray diagnostic apparatus 1b corresponds to an X-ray fluoroscopic diagnosis apparatus for use, for example, in digestive tract angiographic examinations, etc. The X-ray diagnostic apparatus 1b may be an X-ray fluoroscopic diagnosis apparatus for circulatory organs for use, for example, in angiographic examinations.

The X-ray diagnostic apparatus 1b is configured to have both of the technical features of the X-ray diagnostic apparatus 1 according to the first embodiment and the X-ray diagnostic apparatus 1a according to the second embodiment. Specifically, the control circuitry 1000 have each of the functions of the control circuitry 10 and each of the functions of the control circuitry 100. Instead of the second embodiment, the third embodiment or the fourth embodiment may be used.

The control circuitry 1000 is a processor to control, for example, various circuitries and a drive device in the X-ray diagnostic apparatus 1b. The control circuitry 1000 temporarily stores information such as operator's instructions input from the input interface circuitry 9 in an unillustrated memory. The control circuitry 1000 controls the X-ray high-voltage generator 2, X-ray movable diaphragm 3b, and drive device, etc. to implement X-ray imaging and fluoroscopy in accordance with operator's instructions stored in the memory. Also, the control circuitry 1000 controls X-ray image generation processing in the image generation circuitry 7, and image processing in the processing circuitry 11, etc.

Furthermore, the control circuitry 1000 executes (1) various functions for performing settings and control relating to X-ray diaphragm; and (2) various functions for performing settings and control relating to FOV sizes and FOV positions, in accordance with operator's instructions stored in the memory. Examples of the various functions (1) include an FOV size setting function 1000a, a virtual field of view setting function 1000b, a beam-limiting position calculation function 1000c, and a diaphragm control function 1000d, etc. Examples of the various functions (2) include an FOV size setting function 1000a, an FOV position setting function 1000e, a second diaphragm control function 1000f, an FOV position writing function 1000g, and an FOV position restoring function 1000h. The processor of the control circuitry 1000 and the processor of the processing circuitry 11 may be integrated into one processor.

The FOV size setting function 1000a sets any one of FOV size of a plurality of FOV sizes relating to the irradiation field of X-ray. Specifically, the FOV size setting function 1000a sets, for example, a first FOV size (for example, corresponding to a wide field of view M1) of a plurality of FOV sizes relating to the irradiation field of X-ray. At that time, the operator selects a discretional FOV size (or a discretional magnification ratio) by pressing down a switch button of an input interface circuitry 9. As a method of selecting an FOV size, a method of selecting it by touching a touch panel, and a method of selecting it by sound recognition may be used.

The virtual field of view setting function 1000b sets a virtual field of view by operator's operations. Herein, a "virtual field of view" is a field of view that can include an outer side of an X-ray detection region that was not assumed in the past and does not match an irradiation range within which X-ray is actually applied. The "virtual field of view" is synonymous with an image to be displayed on the later-described display. Specifically, the virtual field of view setting function 1000b sets, for example, a virtual field of view having an FOV size set by the FOV size setting function 1000a so as to be able to run over from the X-ray detection region of the X-ray detector 4.

The beam-limiting position calculation function 1000c calculates a beam-limiting position corresponding to the virtual field of view (or a virtual field of view at the FOV position) set by the FOV size setting function 1000a and the virtual field of view setting function 1000c.

The first diaphragm control function 1000d controls the X-ray movable diaphragm 3b based on the set virtual field of view. At that time, the first diaphragm control function 1000d controls the X-ray movable diaphragm 3b so as to apply X-ray to a common region between the set virtual field of view and the X-ray detection region.

The FOV position setting function 1000e sets an FOV position by operator's operations. Specifically, the FOV position setting function 1000e reads out an FOV position corresponding to the FOV size set by the FOV size setting function 1000a from the storage circuitry 12 and to adjust the read FOV position in accordance with operator's operations.

The second diaphragm control function 1000f controls the X-ray movable diaphragm 3b based on a field of view at the FOV position set by the FOV position setting function 1000e.

The FOV position writing function 1000g associates an adjusted final FOV position with the set FOV size and writes, in the storage circuitry 12, etc., the adjusted final FOV position associated with the set FOV size. Specifically, the FOV position writing function 1000g writes the final FOV position, for example, taking a switching setting, by the FOV size setting function 1000a, to a second FOV size different from the set first FOV size, as a trigger.

The FOV position restoring function 1000h reads out an FOV position associated with the FOV size from the storage circuitry 12, etc., taking FOV size that was selected in the past by the FOV size setting function 1000a being reset as a trigger.

Figure 23:
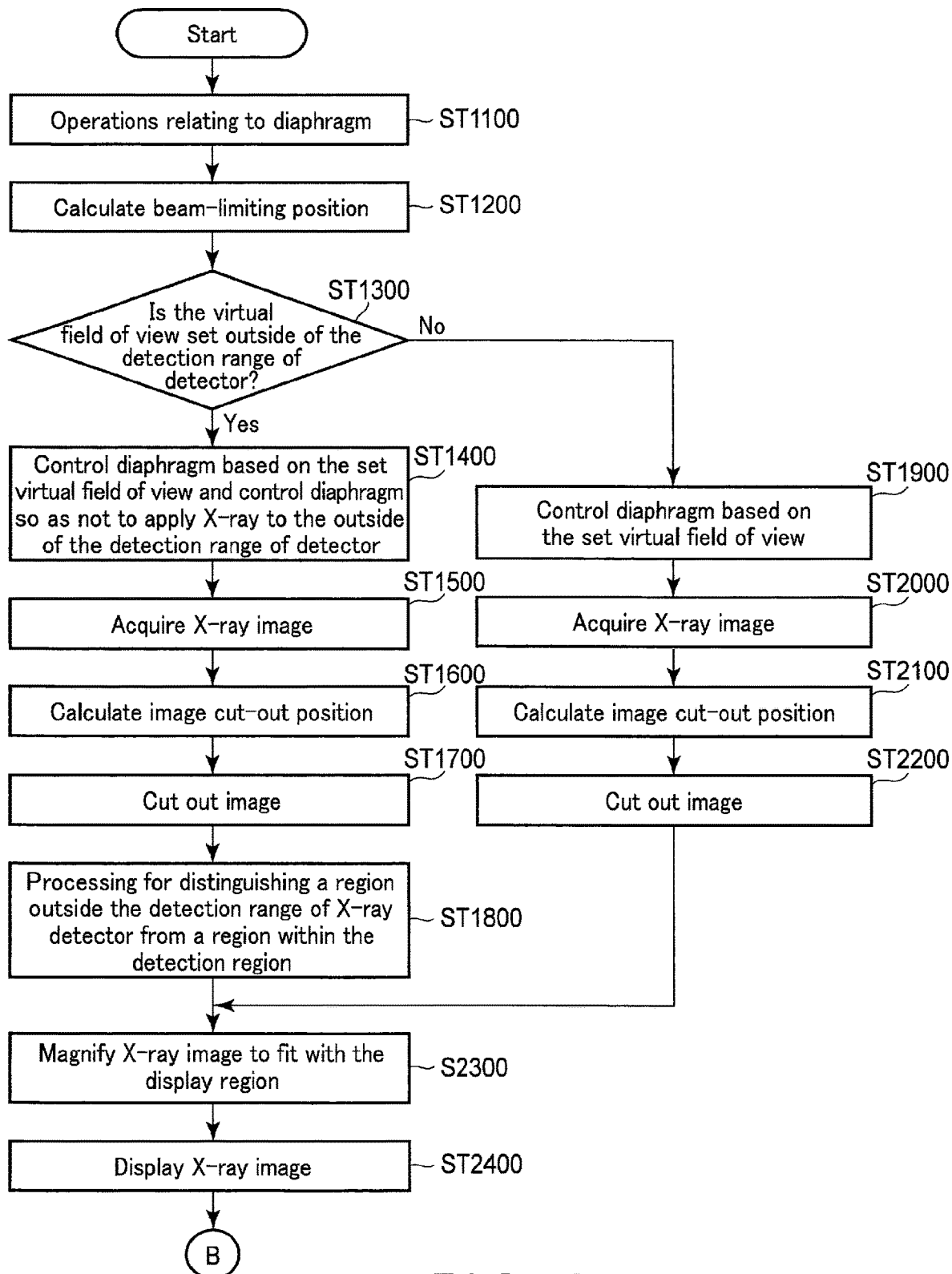
FIG. 23 is a flowchart showing one example of the operations of the X-ray diagnostic apparatus according to the fifth embodiment.
Figure 24:
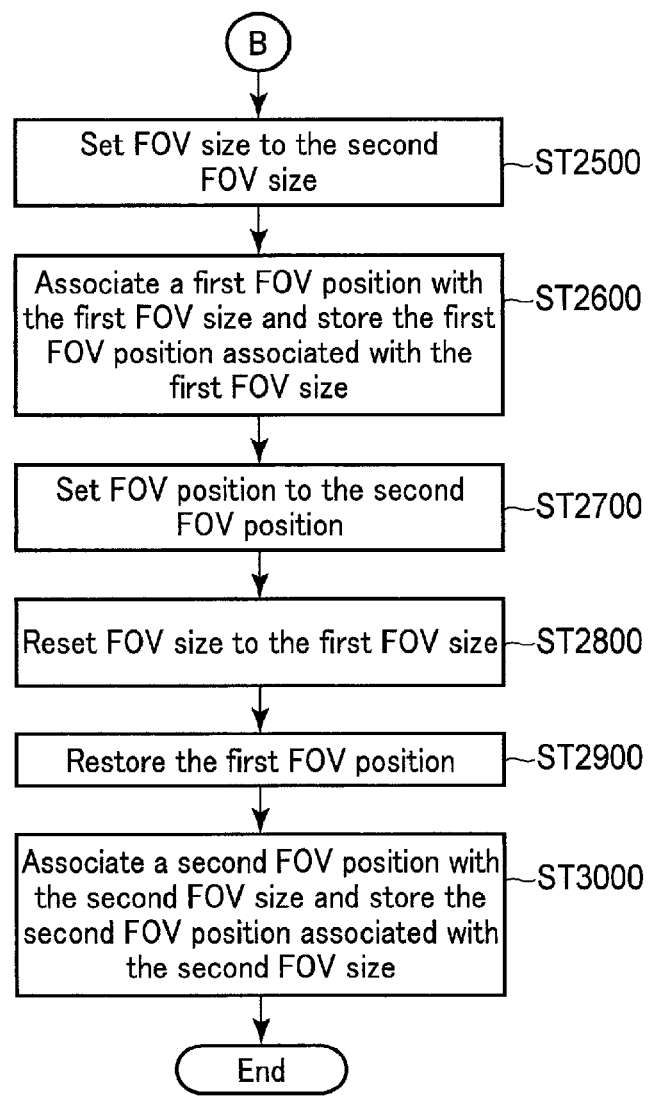
FIG. 24 is a flowchart showing one example of the operations of the X-ray diagnostic apparatus according to the fifth embodiment.

Next, the operations of the X-ray diagnostic apparatus 1b configured as above are described using the flowchart of FIG. 23 and the flowchart of FIG. 24. The following explanations mainly include (1) settings and control relating to X-ray diaphragm by the control circuitry 1000 and the image generation processing by the processing circuitry 11; and (2) settings and control relating to FOV sizes and FOV positions by the control circuitry 1000. Note that the above item (1) corresponds to the flowchart of FIG. 23, and the above item (2) corresponds to the flowchart of FIG. 24.

First, a subject P is placed on the table top 6 of the bed. In the X-ray diagnostic apparatus 1b, a preset examination type and a preset examination name are selected, and imaging conditions associated with the selected examination type and examination name are set, by operator's operations. Thereafter, the X-ray diagnostic apparatus 1b starts X-ray fluoroscopy by operator's operations and starts step ST1100.

(Step ST1100)

The X-ray diagnostic apparatus 1b accepts an operation relating to diaphragm. Specifically, the FOV size setting function 1000a sets any one of a plurality of fields of view by operator's instructions. For example, the FOV size setting function 1000a sets a first FOV size relating to the irradiation field of X-ray. The virtual field of view setting function 1000b sets a virtual field of view (or an FOV position), taking setting of a FOV size as a trigger.

(Step ST1200)

The diaphragm position calculation function 1000c calculates a diaphragm position corresponding to the virtual field of view set in step ST1000 (or a virtual field of view at an FOV position).

(Step ST1300)

The control circuitry 1000 determines whether or not the virtual field of view is set at the outer side (the outer portion of the detection region) of the X-ray detection region of the detector. Specifically, the control circuitry 1000 determines whether or not the beam-limiting position calculated in step ST1200 includes an outer portion of the detection range of the X-ray detector 4. If the beam-limiting position includes the outer portion the detection range of the X-ray detector 4, the process proceeds to ST1400, and if this is not the case, the process proceeds to step ST1900.

(Step ST1400)

The first diaphragm control function 1000*d* controls the X-ray movable diaphragm 3*b*, based on the set virtual field of view (or a field of view at an FOV position, or the calculated beam-limiting position), so as not to apply the X-ray to the outer portion of the detection region of the X-ray detector 4.

(Step ST1500)

The processing circuitry 11 acquires an X-ray image generated by the image generation circuitry 7.

(Step ST1600)

The image cut-out position calculation function 11*a* calculates, as an image cut-out position, a range of the X-ray applied to the X-ray detection region of the X-ray detector 4, based on the beam-limiting position calculated in step ST1200, the position of the X-ray source device 3, and the position of the X-ray detector 4.

(Step ST1700)

The image cut-out function 11*b* cuts out an X-ray image based on the image cut-out position calculated in step ST1600.

(Step ST1800)

The image processing function 11*c* generates a processed image corresponding to the virtual field of view of the set FOV portion and including the X-ray image cut out in step ST1700.

(Step ST1900)

The first diaphragm control function 1000*d* controls the X-ray movable diaphragm 3*b* based on the virtual field of view at the set FOV position (or the calculated beam-limiting position).

(Step ST2000)

The processing circuitry 11 acquires the X-ray image generated by the image generation circuitry 7.

(Step ST2100)

The image cut-out position calculation function 11*a* calculates, as an image cut-out position, a range of the X-ray applied to the X-ray detection region of the X-ray detector 4, based on the beam-limiting position calculated in step ST1200, the position of the X-ray source device 3, and the position of the X-ray detector 4.

(Step ST2200)

The image cut-out function 11*b* cuts out an X-ray image based on the image cut-out position calculated in step ST1600.

(Step ST2300)

The image magnification function 11*d* magnifies the processed image generated in step ST1800 or the X-ray image cut out in step ST220 to fit with the display window of the display.

(Step ST2400)

The display circuitry 13 displays the magnified processed image or X-ray image magnified in step ST2300.

(Step ST2500)

The FOV size setting function 1000*a* sets an FOV size to a second FOV size different from the first FOV size.

(Step ST2600)

The FOV position writing function 1000*g* associates the first FOV position before the setting of switching with the first FOV size and stores the first FOV position and the first FOV size in the storage circuitry 12, etc., taking a setting of switching from the first FOV size to the second FOV size, as a trigger.

(Step ST2700)

The FOV position setting function 1000*e* suitably sets the adjusted FOV position to a second FOV position by operator's operations. The second diaphragm control function 1000*f* controls the X-ray movable diaphragm 3*b*, based on an FOV size and the adjusted FOV position. The adjusted FOV position may be set so as to be able to run off from the X-ray detection region of the X-ray detector by the virtual field of view setting function 1000*b*, instead of the FOV position setting function 1000*e*. At that time, the X-ray movable diaphragm 3*b* is controlled based on the field of view at the adjusted FOV position so as not to apply the X-ray to the outer side portion of the detection range of the X-ray detector 4.

(Step ST2800)

The FOV size setting function 1000*a* resets the FOV size to the first FOV size by operator's operations.

(Step ST2900)

The FOV position restoring function 1000*h* reads out the first FOV position associated with the first FOV size from the storage circuitry 12, taking resetting of the first FOV size by the FOV size setting function 1000*a*, as a trigger. With this configuration, the FOV position restoring function 1000*h* restores the first FOV position. The second diaphragm control function 1000*f* controls the X-ray movable diaphragm 3*b* based on the FOV size and the restored FOV position.

(Step ST3000)

The FOV position writing function 1000*g* associates the second FOV position before resetting with the second FOV size and stores, in the storage circuitry 12, etc., the second FOV position associated with the second FOV size, taking resetting of switching from the second FOV size to the first FOV size by the FOV size setting function 1000*a*, as a trigger.

The order of a series of the processes from the step ST1100 to step ST2400 and the order of a series of the processes from the step ST2500 to step ST3000 may be exchanged with one another.

As described above, according to the fifth embodiment, the X-ray diagnostic apparatus includes a memory that stores an FOV size in association with an FOV position, the FOV size being related to the irradiation field, the FOV position being within the X-ray detection region. The X-ray diagnostic apparatus sets a first FOV size related to the irradiation field of X-ray, and sets a virtual field of view having the first FOV size, the virtual field of view being able to include an outside region of an X-ray detection region and at least a part of the X-ray detection region. The X-ray diagnostic apparatus controls the X-ray movable diaphragm so as to apply the X-ray to a common region between the virtual field of view and the X-ray detection region. Furthermore, the X-ray diagnostic apparatus sets a second FOV size different from the first FOV size, reads out an another FOV position associated with the set second FOV size from the memory, and controls the X-ray movable diaphragm based on the second FOV size and the another FOV position associated with the set second FOV size.

Therefore, since the X-ray diagnostic apparatus according to the fifth embodiment can set a virtual field of view, taking switching of a plurality of FOV sizes, as a trigger, it can continuously display the region of interest at the center of the display screen, even if an outer side region of the X-ray detection region is included in the field of view at the time of magnifying the field of view. Furthermore, this X-ray diagnostic apparatus can maintain FOV positions set in past days, when the FOV size is switched, by means of the configuration in which the X-ray movable diaphragm can be controlled based on a set FOV size and an FOV position which is read out in association with the FOV size.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
   an X-ray movable diaphragm that limits an irradiation field of X-rays generated by an X-ray tube; and
   processing circuitry configured to:
      set an FOV size related to the irradiation field of the X-rays,
      set a virtual field of view having the FOV size as a provisional irradiation field of the X-rays, the virtual field of view being able to include an outside region of an X-ray detection region and at least a part of the X-ray detection region, and
      control the X-ray movable diaphragm based on a positional relationship of the set virtual field of view with the X-ray detection region so as to apply the X-rays to the at least part of the X-ray detection region but not to the outside region of the X-ray detection region for the set virtual field of view.

2. The apparatus according to claim 1, wherein the processing circuitry is further configured to set the FOV size to any of a plurality of prepared FOV sizes.

3. The apparatus according to claim 2, wherein the processing circuitry is further configured to set the virtual field of view, taking as a trigger a switching of the plurality of prepared FOV sizes.

4. The apparatus according to claim 1, wherein the processing circuitry is further configured to set the virtual field of view so that a center of the virtual field of view is positioned within the X-ray detection region.

5. The apparatus according to claim 1, wherein the processing circuitry is further configured to
   generate an X-ray image based on the X-rays detected within the X-ray detection region, and
   generate a display image corresponding to the virtual field of view so that the display image includes the X-ray image and a padding image indicating the outside region of the X-ray detection region.

6. The apparatus according to claim 5, wherein
   the processing circuitry is further configured to generate the padding image as a mesh image of black-and-white bi-level.

7. The apparatus according to claim 5, wherein
   the processing circuitry is further configured to generate the padding image using hue information.

8. The apparatus according to claim 1, further comprising:
   a switch button for selecting the FOV size by operator's operations; and
   a joystick for moving the virtual field of view to a desired position by operator's operations.

9. The X-ray diagnostic apparatus according to claim 1, wherein the processing circuitry is configured to control the X-ray movable diaphragm based on the positional relationship of the set virtual field of view with the X-ray detection region so as to apply the X-rays to a common region between the virtual field of view and the X-ray detection region.

10. The X-ray diagnostic apparatus according to claim 1, wherein
    the processing circuitry is configured to
       determine, based on a positional relationship of the set virtual field of view with the X-ray detection region, whether or not the set virtual field includes an outside region of the X-ray detection region, and
       control the X-ray movable diaphragm based on a determination that the set virtual field includes an outside region of the X-ray detection region so as to apply the X-rays to the part of the X-ray detection region but not to the outside region of the X-ray detection region for the set virtual field of view.

11. An X-ray diagnostic apparatus comprising:
    an X-ray movable diaphragm that limits an irradiation field of X-rays generated by an X-ray tube;
    a memory that stores an FOV size and an FOV position that is associated with the FOV size, the FOV size being associated with a size of the irradiation field, the FOV position indicating a position within an X-ray detection region of an X-ray detector at which a field of view corresponding to the FOV size is to be set; and
    processing circuitry configured to:
       set an FOV size,
       read out, from the memory, the FOV position corresponding to the set FOV size; and
       control the X-ray movable diaphragm to irradiate the X-rays to a region of the X-ray detection region that is defined based on the set FOV size and the read-out FOV position.

12. The apparatus according to claim 11, wherein
    the processing circuitry is further configured to
       adjust the FOV position in response to operator's operations, and
       write the finally adjusted FOV position in association with the set FOV size in the memory.

13. The apparatus according to claim 12, wherein
    the processing circuitry is further configured to write the finally adjusted FOV position, taking as a trigger a setting of switching to an FOV size different from the set FOV size.

14. The apparatus according to claim 12, wherein
    the processing circuitry is further configured to preset an initial position for a specific FOV position among various FOV positions stored in the memory.

15. The apparatus according to claim 14, wherein
    the processing circuitry is further configured to set the initial position in the memory, based on an anatomical position relationship according to each of various types of examination.

16. The apparatus according to claim 14, wherein
    the processing circuitry is further configured to set the initial position in the memory, based on a positional relationship between the initial position and a region corresponding to an entire surface of the X-ray detection region.

17. The apparatus according to claim 11, wherein
    the processing circuitry is further configured to store X-ray conditions related to each of the FOV sizes in association with each of the FOV sizes and each of the FOV positions.

18. The apparatus according to claim 11, wherein
the processing circuitry is further configured to
store a predetermined FOV size in association with a plurality of FOV positions, and;
read out, from the memory, one of the plurality of FOV positions corresponding to the predetermined FOV size in rotation, every time the predetermined FOV size is set in succession.

19. The apparatus according to claim 11, wherein
the processing circuitry is further configured to generate a reference image corresponding to the entire surface of the X-ray detection region and indicating one or more FOV positions corresponding to the set FOV size.

20. The apparatus according to claim 19, wherein
the processing circuitry is further configured to generate the reference image using an X-ray image preliminarily acquired with an FOV size corresponding to the entire surface of the X-ray detection region by superimposing, on the X-ray image, one or more frame lines representing a field of view corresponding to the set FOV size.

21. The apparatus according to claim 20, wherein
the processing circuitry is further configured to perform processing for making a line type of a frame line representing a field of view corresponding to the set FOV size that is currently selected different from a line type of frame lines other than the frame line.

22. An X-ray diagnostic apparatus comprising:
an X-ray movable diaphragm that limits an irradiation field of X-rays generated by an X-ray tube;
a memory that stores an FOV size and an FOV position that is associated with the FOV size, the FOV size being associated with a size of the irradiation field, the FOV position indicating a position within an X-ray detection region of an X-ray detector at which a field of view corresponding to the FOV size is to be set; and
processing circuitry configured to:
set a first FOV size related to the irradiation field of the X-rays,
set a virtual field of view having the first FOV size as a provisional irradiation field of the X-rays, the virtual field of view being able to include an outside region of an X-ray detection region and at least a part of the X-ray detection region,
control the X-ray movable diaphragm based on a positional relationship of the virtual field of view with the X-ray detection region so as to apply the X-rays to the at least part of the X-ray detection region but not to the outside region of the X-ray detection region for the set virtual field of view,
set a second FOV size different from the first FOV size, and read out, from the memory, another FOV position corresponding to the set second FOV size, and
control the X-ray movable diaphragm to irradiate the X-rays to a region of the X-ray detection region that is defined based on the set second FOV size and the another FOV position corresponding to the set second FOV size.

* * * * *